US011850010B2

(12) United States Patent
Moctezuma de la Barrera

(10) Patent No.: US 11,850,010 B2
(45) Date of Patent: *Dec. 26, 2023

(54) WORKFLOW SYSTEMS AND METHODS FOR ENHANCING COLLABORATION BETWEEN PARTICIPANTS IN A SURGICAL PROCEDURE

(71) Applicant: MAKO Surgical Corp., Weston, FL (US)

(72) Inventor: José Luis Moctezuma de la Barrera, Freiburg (DE)

(73) Assignee: MAKO Surgical Corp., Weston, FL (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/412,937

(22) Filed: Aug. 26, 2021

(65) Prior Publication Data

US 2021/0391071 A1 Dec. 16, 2021

Related U.S. Application Data

(63) Continuation of application No. 16/256,626, filed on Jan. 24, 2019, now Pat. No. 11,114,199.

(Continued)

(51) Int. Cl.
*A61B 34/00* (2016.01)
*G16H 40/63* (2018.01)
(Continued)

(52) U.S. Cl.
CPC .............. *A61B 34/25* (2016.02); *A61B 34/10* (2016.02); *A61B 34/20* (2016.02); *A61B 90/36* (2016.02);
(Continued)

(58) Field of Classification Search
CPC ......... A61B 34/10; A61B 34/20; A61B 34/25; G16H 40/00; G16H 40/20; G16H 40/63
(Continued)

(56) References Cited

U.S. PATENT DOCUMENTS

| 5,603,318 A | 2/1997 | Heilbrun et al. |
| 6,379,302 B1 | 4/2002 | Kessman et al. |

(Continued)

FOREIGN PATENT DOCUMENTS

| WO | 2004001569 A2 | 12/2003 |
| WO | 2005017729 A2 | 2/2005 |

(Continued)

OTHER PUBLICATIONS

Popescu, Diana et al.; Workflow for Additive Manufacturing of an Individualized Surgical Template; Proceedings in Manufacturing Systems 10.3: 131-140. University "Politehnica" of Bucharest, Machine and Manufacturing Systems Department and Association ICMAS. (2015) (Year: 2015).*

*Primary Examiner* — Hiep V Nguyen
(74) *Attorney, Agent, or Firm* — Howard & Howard Attorneys PLLC

(57) ABSTRACT

A surgical workflow system for assisting a surgical procedure comprises a workflow controller. The workflow controller is configured to access a pre-scripted workflow having a plurality of workflow steps associated with the surgical procedure, obtain camera video data of the surgical procedure, monitor the surgical procedure from the camera video data, predict occurrence of an anticipated deviation from one or more of the workflow steps of the pre-scripted workflow, generate event information to address the predicted occurrence of the anticipated deviation, and automatically respond to the predicted occurrence of the anticipated deviation by being configured to transmit the event information to (Continued)

a participant of the surgical procedure through an information conveyor device.

16 Claims, 13 Drawing Sheets

Related U.S. Application Data

(60) Provisional application No. 62/621,748, filed on Jan. 25, 2018.

(51) Int. Cl.

| | | |
|---|---|---|
| *A61B 34/10* | (2016.01) | |
| *A61B 34/20* | (2016.01) | |
| *G02B 27/01* | (2006.01) | |
| *G06T 7/70* | (2017.01) | |
| *G06T 19/00* | (2011.01) | |
| *A61B 90/00* | (2016.01) | |
| *G06F 18/00* | (2023.01) | |
| *H04N 23/00* | (2023.01) | |
| *G16H 40/20* | (2018.01) | |
| *G16H 80/00* | (2018.01) | |
| *A61B 17/00* | (2006.01) | |
| *A61B 90/50* | (2016.01) | |
| *A61B 34/30* | (2016.01) | |

(52) U.S. Cl.
CPC ........... *G02B 27/017* (2013.01); *G06F 18/00* (2023.01); *G06T 7/70* (2017.01); *G06T 19/006* (2013.01); *G16H 40/63* (2018.01); *H04N 23/00* (2023.01); *A61B 34/30* (2016.02); *A61B 2017/00115* (2013.01); *A61B 2017/00119* (2013.01); *A61B 2034/105* (2016.02); *A61B 2034/2048* (2016.02); *A61B 2034/2055* (2016.02); *A61B 2034/2057* (2016.02); *A61B 2034/2059* (2016.02); *A61B 2034/2065* (2016.02); *A61B 2034/252* (2016.02); *A61B 2034/254* (2016.02); *A61B 2034/256* (2016.02); *A61B 2034/258* (2016.02); *A61B 2090/365* (2016.02); *A61B 2090/372* (2016.02); *A61B 2090/502* (2016.02); *G16H 40/20* (2018.01); *G16H 80/00* (2018.01)

(58) Field of Classification Search
USPC .......................................................... 705/3
See application file for complete search history.

(56) References Cited

U.S. PATENT DOCUMENTS

| | | | |
|---|---|---|---|
| 7,331,929 B2 | 2/2008 | Morita et al. | |
| 7,501,995 B2 | 3/2009 | Morita et al. | |
| 7,567,833 B2 | 7/2009 | Moctezuma De La Barrera et al. | |
| 7,573,439 B2 | 8/2009 | Lau et al. | |
| 7,576,757 B2 | 8/2009 | Kariathungal et al. | |
| 7,725,162 B2 | 5/2010 | Malackowski et al. | |
| 7,726,564 B2 | 6/2010 | Goldbach | |
| 7,738,684 B2 | 6/2010 | Kariathungal et al. | |
| 7,813,784 B2 | 10/2010 | Marquart et al. | |
| 8,004,229 B2 | 8/2011 | Nowlin et al. | |
| 8,010,180 B2 | 8/2011 | Quaid et al. | |
| 8,036,917 B2 | 10/2011 | Kariathungal et al. | |
| 8,217,759 B2 | 7/2012 | Tessier | |
| 8,320,612 B2 | 11/2012 | Knobel et al. | |
| 8,548,629 B2 | 10/2013 | Ortmaier et al. | |
| 8,641,621 B2 | 2/2014 | Razzaque et al. | |
| 9,119,655 B2 | 9/2015 | Bowling et al. | |
| 9,119,670 B2 | 9/2015 | Yang et al. | |
| 9,364,294 B2 | 6/2016 | Razzaque et al. | |
| 9,645,785 B1 | 5/2017 | Hannaford et al. | |
| 9,668,768 B2 | 6/2017 | Piron et al. | |
| 11,114,199 B2 | 9/2021 | Moctezuma De La Barrera | |
| 2002/0082498 A1 | 6/2002 | Wendt et al. | |
| 2003/0097060 A1 | 5/2003 | Yanof et al. | |
| 2003/0210812 A1 | 11/2003 | Khamene et al. | |
| 2004/0034282 A1 | 2/2004 | Quaid | |
| 2005/0203384 A1 | 9/2005 | Sati et al. | |
| 2005/0251168 A1 | 11/2005 | Hess et al. | |
| 2006/0020915 A1* | 1/2006 | Lloyd .................. G16H 70/20 717/111 |
| 2006/0074711 A1 | 4/2006 | Mahesh et al. | |
| 2006/0109238 A1 | 5/2006 | Lau et al. | |
| 2006/0139318 A1 | 6/2006 | Kariathungal et al. | |
| 2006/0139319 A1 | 6/2006 | Kariathungal et al. | |
| 2006/0149418 A1 | 7/2006 | Anvari | |
| 2007/0078678 A1 | 4/2007 | DiSilvestro et al. | |
| 2008/0120141 A1 | 5/2008 | Kariathungal et al. | |
| 2014/0022353 A1 | 1/2014 | Hamersma et al. | |
| 2014/0200621 A1 | 7/2014 | Malackowski et al. | |
| 2014/0276855 A1 | 9/2014 | de la Barrera et al. | |
| 2015/0141826 A1* | 5/2015 | Beymer ................ G16H 40/20 600/407 |
| 2015/0332196 A1* | 11/2015 | Stiller ................... G16H 70/20 705/2 |
| 2015/0366624 A1 | 12/2015 | Kostrzewski et al. | |
| 2016/0378939 A1 | 12/2016 | Baumberger et al. | |
| 2017/0000575 A1 | 1/2017 | Griffiths et al. | |
| 2017/0027654 A1 | 2/2017 | Frimer et al. | |
| 2017/0065352 A1 | 3/2017 | Razzaque et al. | |
| 2017/0109936 A1 | 4/2017 | Powderly et al. | |
| 2017/0151021 A1 | 6/2017 | Quaid, III | |
| 2018/0296297 A1 | 10/2018 | Moloney et al. | |
| 2019/0013099 A1 | 1/2019 | Esterberg et al. | |
| 2019/0228859 A1 | 7/2019 | Moctezuma de la Barrera | |
| 2019/0231433 A1 | 8/2019 | Amanatullah | |

FOREIGN PATENT DOCUMENTS

| | | | |
|---|---|---|---|
| WO | 2012062872 A1 | 5/2012 | |
| WO | 2014146107 A1 | 9/2014 | |
| WO | 2015143067 A1 | 9/2015 | |
| WO | 2016042705 A1 | 3/2016 | |
| WO | 2016071244 A2 | 5/2016 | |
| WO | 2016102336 A1 | 6/2016 | |
| WO | 2017070121 A1 | 4/2017 | |
| WO | 2017075541 A1 | 5/2017 | |
| WO | WO-2017147596 A1 * | 8/2017 | ............ A61B 34/00 |

* cited by examiner

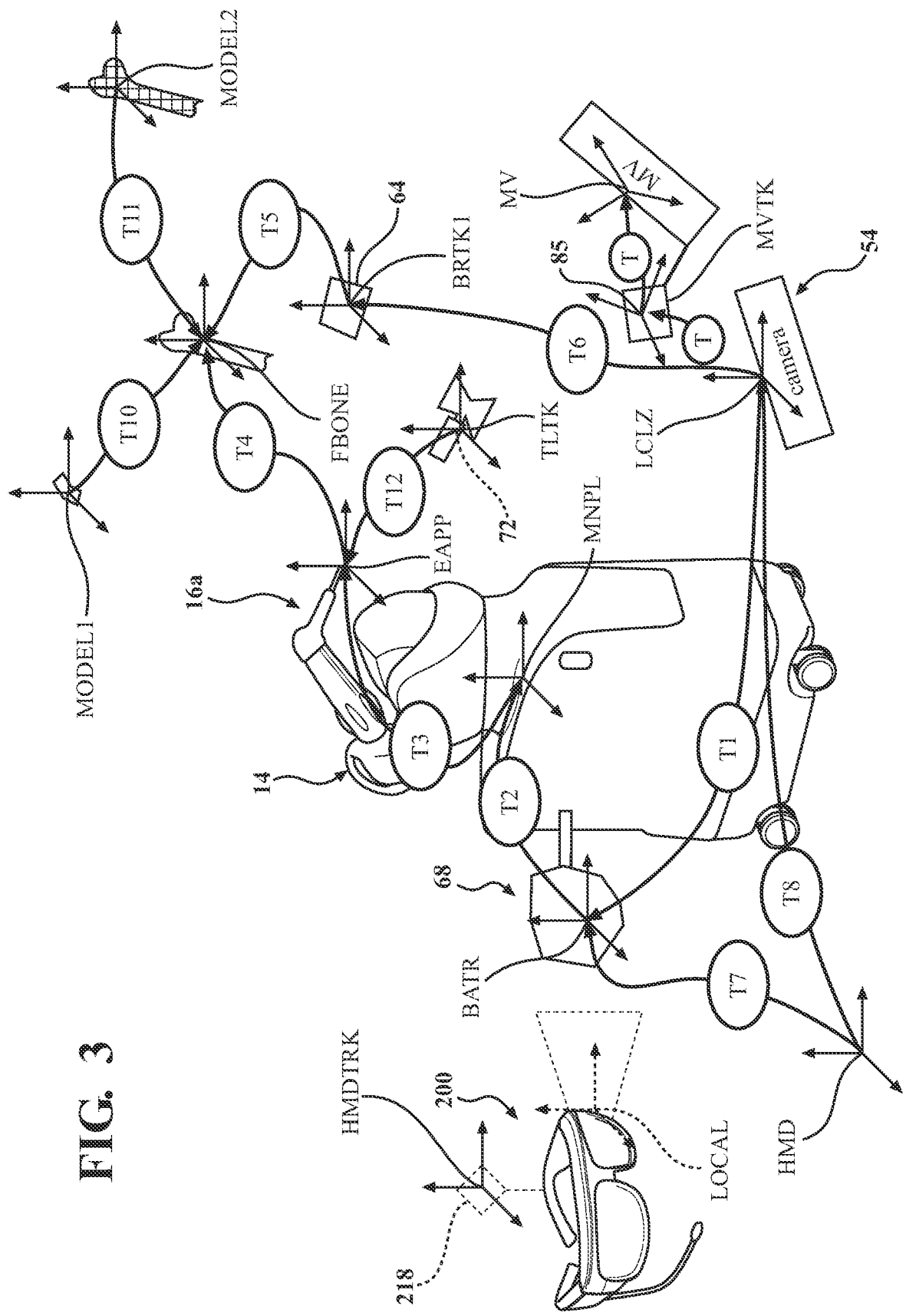

WORKFLOW SYSTEMS AND METHODS FOR ENHANCING COLLABORATION BETWEEN PARTICIPANTS IN A SURGICAL PROCEDURE

RELATED APPLICATIONS

This application is a continuation of U.S. patent application Ser. No. 16/256,626, filed on Jan. 24, 2019, which claims priority to and the benefit of U.S. Provisional Patent Application No. 62/621,748, filed on Jan. 25, 2018, the contents of which are hereby incorporated herein by reference in their entirety.

BACKGROUND

There are a number of active participants forming a surgical team for a typical surgical procedure, often including a surgeon, one or more assistants, a scrub nurse, a circulating nurse, and an operating room (OR) technician. The surgical team carries out the surgical procedure by performing a specific, pre-scripted surgical workflow. In some instances, however, the surgical team will deviate from the pre-scripted surgical workflow to accommodate unforeseen operative intricacies, technical difficulties or other events that may require immediate action.

One of the key characteristics of high performing surgical teams is the ability of the participants to foresee, at every step of the surgical procedure, what the next event of the surgical process will be and to provide appropriate measures and actions for an undisrupted and seamless flow of the surgical procedure. However, there is a lack of suitable systems and methods to assist surgical teams in achieving such high performance. Thus, there is a need in the art for workflow systems and methods to assist surgical teams.

SUMMARY

A surgical workflow system is provided for performing a surgical procedure. The surgical workflow system for assisting a surgical procedure comprises a workflow controller. The workflow controller is configured to access a pre-scripted workflow having a plurality of workflow steps associated with the surgical procedure, obtain camera video data of the surgical procedure, monitor the surgical procedure from the camera video data, predict occurrence of an anticipated deviation from one or more of the workflow steps of the pre-scripted workflow, generate event information to address the predicted occurrence of the anticipated deviation, and automatically respond to the predicted occurrence of the anticipated deviation by being configured to transmit the event information to a participant of the surgical procedure through an information conveyor device.

A method of operating a surgical workflow system for assisting a surgical procedure is provided. The surgical workflow system comprises a workflow controller configured to perform the steps of accessing a pre-scripted workflow having a plurality of workflow steps associated with the surgical procedure, obtaining camera video data of the surgical procedure, monitoring the surgical procedure from the camera video data, predicting an occurrence of an anticipated deviation from one or more of the workflow steps of the pre-scripted workflow generating event information to address the predicted occurrence of the anticipated deviation, and automatically responding to the predicted occurrence of the anticipated deviation by transmitting the event information to a participant of the surgical procedure through an information conveyor device.

BRIEF DESCRIPTION OF THE DRAWINGS

Advantages of the present disclosure will be readily appreciated as the same becomes better understood by reference to the following detailed description when considered in connection with the accompanying drawings.

FIG. 3 illustrates a plurality of transformations between various coordinate systems.

DETAILED DESCRIPTION

Figure 1:
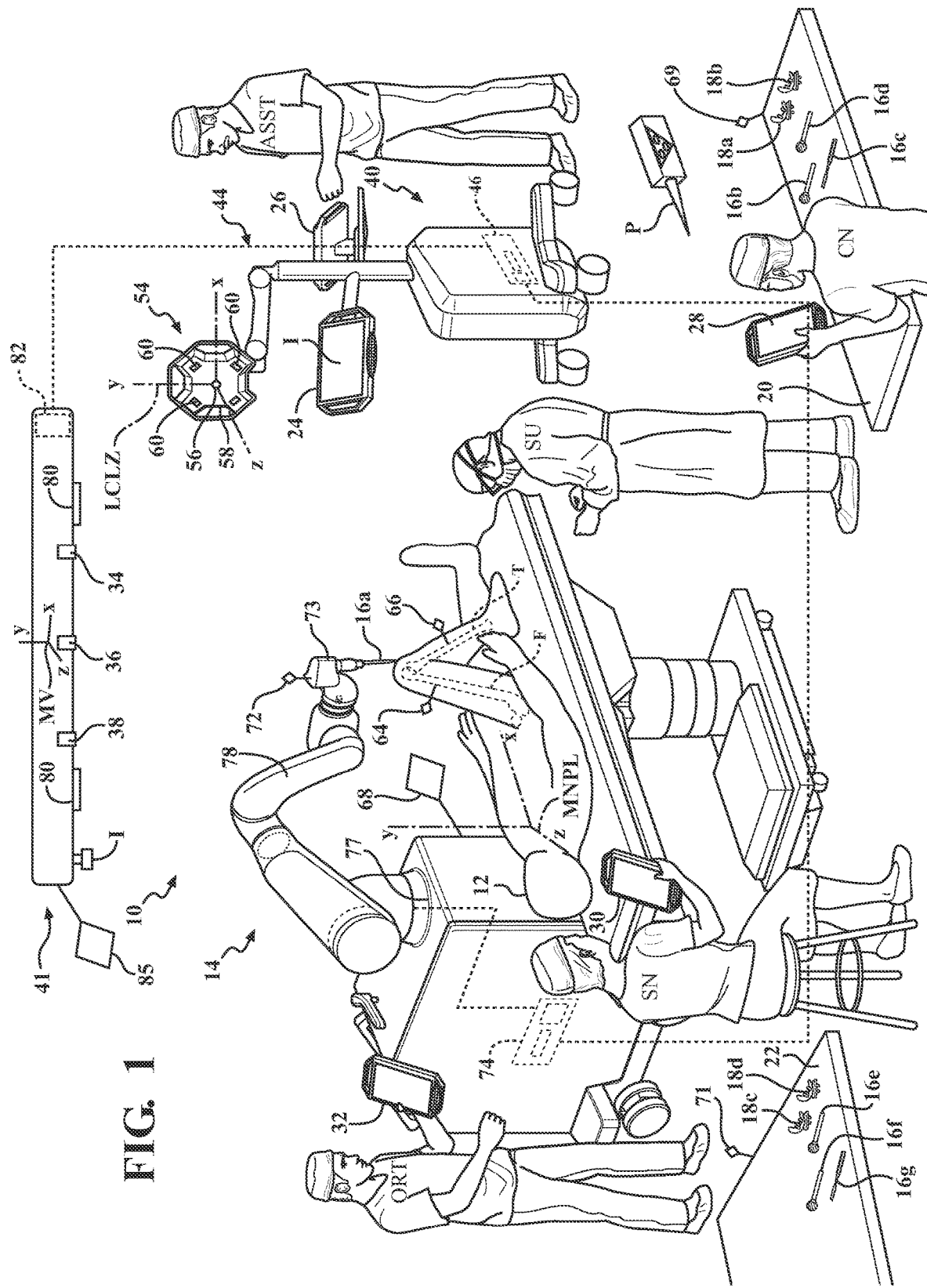
FIG. 1 is a perspective view of an operating environment illustrating various participants and information conveyor devices for each of the participants.

FIG. 1 depicts a surgical workflow system 10 for enhancing collaboration between active participants of a surgical team during a surgical procedure on a patient 12. The surgical workflow system 10 is shown in a surgical environment such as an operating room of a medical facility. In the embodiment shown, the workflow system 10 works in conjunction with various surgical objects initially arranged in the operating room according to a pre-operative surgical plan. Such objects include, for example, the participants, the patient 12, a femur F and a tibia T of the patient 12, a manipulator 14, surgical tools 16a, 16b, 16c, 16d, 16e, 16f, 16g of various types, shapes, and/or sizes, implants 18a, 18b, 18c, 18d of various types, shapes, and/or sizes, circulating tables 20, 22, and the like.

In the embodiment shown in FIG. 1, there are five active participants forming the surgical team, including a surgeon SU, an assistant ASST, a circulating nurse CN, a scrub nurse SN, and an operating room (OR) technician ORT. Other types/numbers of participants are also contemplated. The surgical team carries out the surgical procedure by performing a specific, pre-scripted surgical workflow comprising a plurality of workflow steps associated with the surgical procedure. In some instances, however, the surgical team will deviate from the pre-scripted surgical workflow to accommodate unforeseen operative intricacies, technical difficulties or other change events that may require immediate action. The workflow system 10 operates to locate and/or track one or more of the objects mentioned above during the surgical procedure in anticipation of such change events so that the workflow system 10 can assist the surgical team in performing immediate action in response to such change events.

The workflow system 10 comprises a plurality of information conveyor devices. The information conveyor devices shown in FIG. 1 comprise displays 24, 26, 28, 30, 32 and projectors 34, 36, 38. The information conveyor devices are arranged in the operating room so that one or more of the information conveyor devices are associated with each of the participants. For instance, the displays 24, 26, 28, 30, 32 are strategically placed in the operating room for being viewed by the surgeon SU, the assistant ASST, the circulating nurse CN, the scrub nurse SN, and the operating room technician ORT, respectively. The displays 24, 26 are part of a navigation system 40 described further below. The display 28 is mounted to the circulating table 20 or other suitable structure and/or hand-held by the circulating nurse CN, and may be any suitable form of display, including displays of portable electronic devices (e.g., tablets, smart phones, iPhone®, iPad®, etc). The display 30 is mounted to an operating table or other suitable structure and/or hand-held by the scrub nurse SN, and may be any suitable form of display, including displays of portable electronic devices (e.g., tablets, smart phones, iPhone®, iPad®, etc). The display 32 is mounted to the manipulator 14 or other suitable structure and/or hand-held by the operating room technician ORT, and may be any suitable form of display, including displays of portable electronic devices (e.g., tablets, smart phones, iPhone®, iPad®, etc). It should be appreciated that the displays 24, 26, 28, 30, 32 could be mounted in other locations and/or may comprise displays of any suitable type. Other forms of information conveyor devices could also be used. For example, the information conveyor devices may comprise one or more of head-mounted displays HMDs described below and shown in FIG. 1A, audible feedback devices such as speakers SPK, tactile feedback devices such as piezoelectric elements, or other visual feedback devices such as laser pointers, laser line/plane generators, LEDs, and other light sources.

The information conveyor devices can use one or multiple sensory channels, such as visual, audio, and tactile, but could also be olfactory or other sensory modalities, such as thermoceptive, nociceptive or mechanoceptive to convey contextually personalized information to achieve a common goal in a collaborative fashion. Directional projected sound may be provided, such as a system that projects sound only audible at a specific location in the operating room so that only one or two of the participants are able to hear it.

Referring back to FIG. 1, the projectors 34, 36, 38 may be overhead projectors or wearable projectors that are correlated to the same coordinate system (e.g., the localizer coordinate system LCLZ as described below) and are aware of the location of the objects in the localizer coordinate system LCLZ, thus being able to project personalized contextual information onto relevant objects. Systems and methods for employing projectors to provide information are disclosed in U.S. Pat. No. 7,567,833, entitled "Enhanced Illumination Device And Method," which is hereby incorporated herein by reference. Wearable mechano-thermal actuators could also be used to direct a participant's awareness towards an occurring or anticipated event, e.g., a wearable headband with vibratory elements and/or peltier elements (heat-cold) to indicate a direction or flow.

Figure 2:
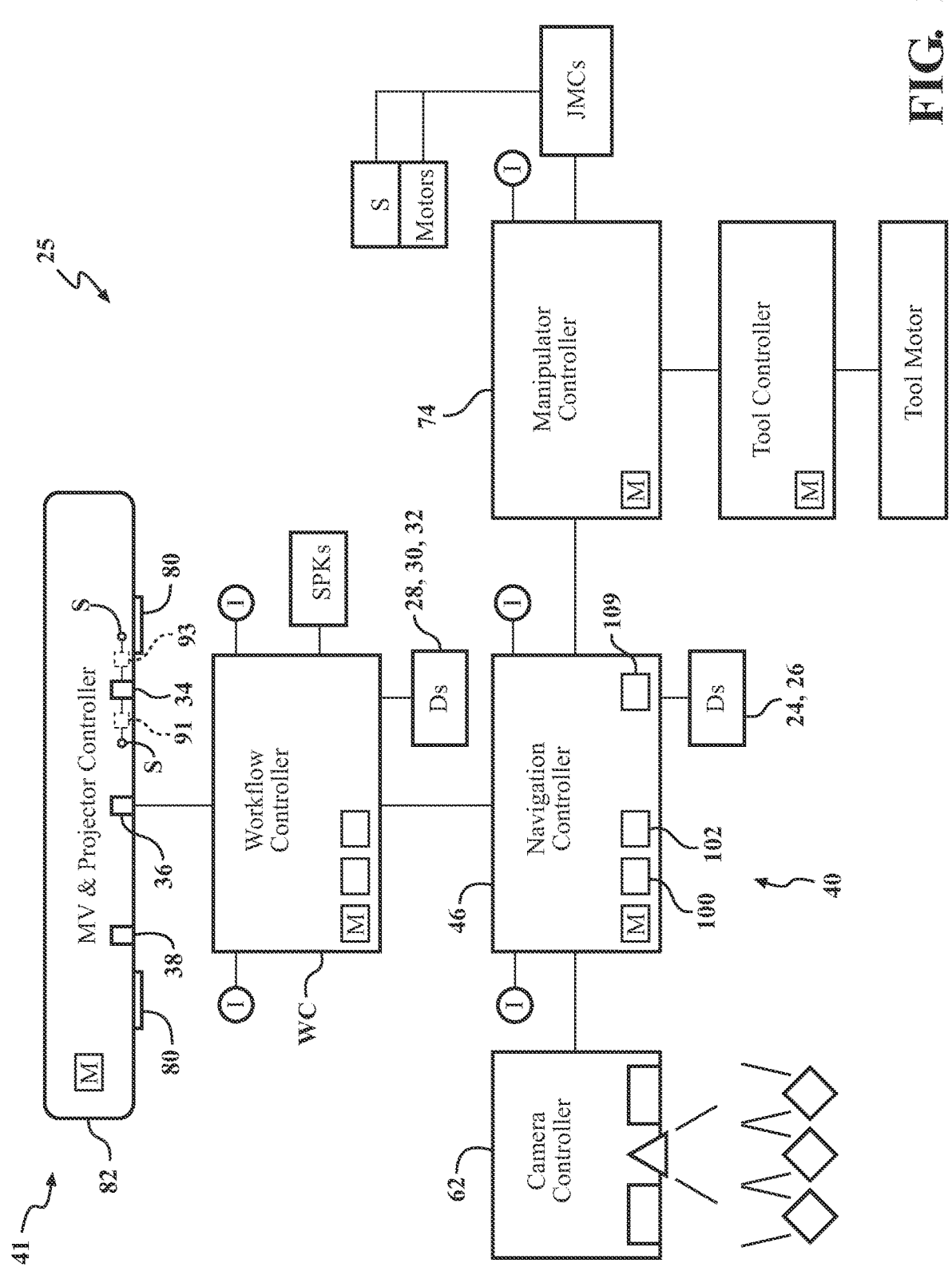
FIG. 2 is a schematic view of a workflow control system.

Referring to FIG. 2, a workflow control system 25 is shown. The workflow control system 25 comprises a workflow controller WC that assists the surgical team by storing, generating, and outputting information to the participants regarding the pre-scripted surgical workflow. In some cases, the workflow steps of the pre-scripted surgical workflow may be stored in a database located in memory M in the workflow controller WC and/or in one or more other locations in the workflow control system 25 to be accessed and distributed to the participants, such as through instructions displayed to the participants on the displays 24, 26, 28, 30, 32.

When the surgical team needs to deviate from the pre-scripted surgical workflow to accommodate change events, the workflow controller WC operates to determine the nature of the change event, access change event information in the database stored in the memory M, and output the change event information to the participants. This includes displaying different information to the different participants so that the change event can be addressed in a seamless fashion without significant disruption to the pre-scripted surgical workflow.

The workflow controller WC is configured to receive as input the pre-operative surgical plan that was created pre-operatively (but can also be created intra-operatively) and stores the pre-operative surgical plan in the memory M. The workflow controller WC determines the pre-scripted surgical workflow based on the pre-operative surgical plan and accesses the pre-scripted surgical workflow from the database stored in the memory M. Once the pre-scripted surgical workflow is established, the workflow controller WC provides instructions to one or more of the participants (e.g., using the information conveyor devices) on how to arrange the plurality of objects based on the pre-scripted surgical workflow. For example, the workflow controller WC may provide instructions on how to arrange the patient 12, including the patient's femur F and tibia T, the manipulator 14, the surgical tools 16a, 16b, 16c, 16d, 16e, 16f, 16g, the implants 18a, 18b, 18c, 18d, the circulating tables 20, 22, and the like. Notably, the plurality of objects arranged in the operating room may include those required for the pre-scripted surgical workflow and additional, contingent objects. Contingent objects are those objects that the database identifies as having a chance of being required during typical change events associated with such surgical procedures. For example, tools 16a, 16b, and 16g may be required according to the pre-scripted surgical workflow, but tools 16c, 16d, etc. may be provided as contingent objects.

With the objects properly arranged, the workflow controller WC monitors the surgical procedure and identifies change events that indicate a deviation from the pre-scripted workflow, e.g., the manipulator 14 needs servicing, the implant size has changed, the tool 16a is worn or broken, additional treatment is required, etc. When the workflow controller WC detects that a change event has occurred, the workflow controller WC determines/accesses change event information tailored to the different participants based on the change event and transmits the change event information to the participants through the plurality of information conveyor devices so that different change event information can be conveyed to the different participants.

The workflow controller WC is configured to provide change event information to each of the different participants by one or more of: displaying the change event information on one of the displays 24, 26, 28, 30, 32; displaying the change event information on one of the head-mounted displays HMDs; transmitting the change event information through one of the speakers SPK; transmitting the change event information through one of the tactile feedback devices; projecting the change event information with one of the projectors 34, 36, 38; illuminating one or more of the objects with one or more light sources; and other suitable information conveying methods.

In one embodiment, the change event information is associated with one or more of the plurality of objects and the workflow controller WC operates to provide the change event information based on the locations of the one or more of the plurality of objects. The workflow controller WC is in communication with one or more locators to determine locations of the various objects in the operating room. In the embodiment shown, the locators comprise the surgical navigation system 40 and a machine vision system 41.

Referring briefly to FIG. 1, the surgical navigation system 40 is set up to locate and/or track movement of some of the objects such as the manipulator 14, surgical tool 16a, the femur F, the tibia T, and tables 20, 22. The navigation system 40 locates and/or tracks these objects for purposes of displaying their locations (e.g., positions and/or orientations) to one or more of the participants.

The navigation system 40 includes one or more computer cart assemblies 44 that houses one or more navigation controllers 46. A navigation interface is in operative communication with the navigation controller 46. The navigation interface includes the displays 24, 26 adjustably mounted to the computer cart assembly 44 or mounted to separate carts. Input devices I (see FIG. 2) such as a keyboard and mouse can be used to input information into the navigation controller 46 or otherwise select/control certain aspects of the navigation controller 46. Other input devices I are contemplated including a touch screen, voice-activation, gesture sensors, and the like.

A surgical navigation localizer 54 communicates with the navigation controller 46. In the embodiment shown, the localizer 54 is an optical localizer and includes a camera unit 56. In other embodiments, the localizer 54 employs other modalities for tracking, e.g., radio frequency (RF), ultrasonic, electromagnetic, and/or inertial, and the like. The camera unit 56 has a housing 58 comprising an outer casing that houses one or more optical position sensors 60. In some embodiments, at least two optical sensors 60 are employed, preferably three or four. The optical sensors 60 may be separate charge-coupled devices (CCD). In one embodiment three, one-dimensional CCDs are employed. Two-dimensional or three-dimensional sensors could also be employed. It should be appreciated that in other embodiments, separate camera units, each with a separate CCD, or two or more CCDs, could also be arranged around the operating room. The CCDs detect light signals, such as infrared (IR) signals.

Camera unit 56 is mounted on an adjustable arm to position the optical sensors 60 with a field-of-view of the below discussed trackers that, ideally, is free from obstructions. In some embodiments, the camera unit 56 is adjustable in at least one degree of freedom by rotating about a rotational joint. In other embodiments, the camera unit 56 is adjustable about two or more degrees of freedom.

The camera unit 56 includes a camera controller 62 (see FIG. 2) in communication with the optical sensors 60 to receive signals from the optical sensors 60. The camera controller 62 communicates with the navigation controller 46 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 60 communicate directly with the navigation controller 46.

Position and orientation signals and/or data are transmitted to the navigation controller 46 for purposes of locating and/or tracking the objects. The computer cart assembly 44, displays 24, 26, and camera unit 56 may be like those described in U.S. Pat. No. 7,725,162 to Malackowski, et al. issued on May 25, 2010, entitled "Surgery System," hereby incorporated by reference.

The navigation controller 46 can be a personal computer or laptop computer. Navigation controller 46 has the displays 24, 26, central processing unit (CPU) and/or other processors, memory (not shown), and storage (not shown). The navigation controller 46 is loaded with software as described below. The software, for example, converts the signals received from the camera unit 56 into data representative of the position and orientation of the objects being located/tracked. In some embodiments, the navigation controller 46 operates as the workflow controller WC.

Navigation system 40 is operable with a plurality of tracking devices 64, 66, 68, 69, 71, 72 also referred to herein as trackers. In the illustrated embodiment, one tracker 64 is firmly affixed to the femur F of the patient and another tracker 66 is firmly affixed to the tibia T of the patient. Trackers 64, 66 may be attached to the femur F and tibia T in the manner shown in U.S. Pat. No. 7,725,162, hereby incorporated by reference. Trackers 64, 66 could also be mounted like those shown in U.S. Patent Application Pub. No. 2014/0200621, filed on Jan. 16, 2014, entitled, "Navigation Systems and Methods for Indicating and Reducing Line-of-Sight Errors," hereby incorporated by reference herein. In additional embodiments, a tracker (not shown) is attached to the patella to track a position and orientation of the patella. In yet further embodiments, the trackers 64, 66 could be mounted to other tissue types or parts of the anatomy.

A base tracker 68 is shown coupled to the manipulator 14. In other embodiments, a tool tracker 72 may be substituted for the base tracker 68 or used in addition to the base tracker 68. The tool tracker 72 may be integrated into a surgical tool 73 during manufacture or may be separately mounted to the surgical tool 73 (or to an end effector attached to the manipulator 14 of which the surgical tool 73 forms a part) in preparation for surgical procedures. The working end of the surgical tool 73, which is being tracked by virtue of the base tracker 68, may be referred to herein as an energy applicator, a surgical accessory, a cutting accessory, or may be referred to as surgical tool 16a, and may be a rotating bur, electrical ablation device, probe, or the like. Trackers 69, 71 may also be fixed to the circulating tables 20, 22 to locate the circulating tables 20, 22.

In the embodiment shown, the surgical tool 73, and by extension the surgical tool 16a, is attached to the manipulator 14 to be supported by the manipulator 14. Such an arrangement is shown in U.S. Pat. No. 9,119,655, entitled, "Surgical Manipulator Capable of Controlling a Surgical Instrument in Multiple Modes," the disclosure of which is hereby incorporated by reference.

The optical sensors 60 of the localizer 54 receive light signals from the trackers 64, 66, 68, 69, 71, 72. In the illustrated embodiment, the trackers 64, 66, 68, 69, 71, 72 are passive trackers. In this embodiment, each tracker 64, 66, 68, 69, 71, 72 has at least three passive tracking elements or markers (e.g., reflectors) for transmitting light signals (e.g., reflecting light emitted from the camera unit 56) to the optical sensors 60. In other embodiments, active tracking markers can be employed. The active markers can be, for example, light emitting diodes transmitting light, such as infrared light. Active and passive arrangements are possible.

The navigation controller 46 includes a navigation processor. It should be understood that the navigation processor could include one or more processors to control operation of the navigation controller 46. The processors can be any type of microprocessor or multi-processor system. The term processor is not intended to limit the scope of any embodiment to a single processor.

The camera unit 56 receives optical signals from the trackers 64, 66, 68, 69, 71, 72 and outputs to the navigation controller 46 signals relating to the position of the tracking markers of the trackers 64, 66, 68, 69, 71, 72 relative to the localizer 54. Based on the received optical signals, navigation controller 46 generates data indicating the relative positions and orientations of the trackers 64, 66, 68, 69, 71, 72 relative to the localizer 54. In one version, the navigation controller 46 uses well known triangulation methods for determining location data.

Prior to the start of the surgical procedure, additional data are loaded into the navigation controller 46. Based on the position and orientation of the trackers 64, 66, 68, 69, 71, 72 and the previously loaded data, navigation controller 46 determines the position of the surgical tool 16*a* (e.g., the centroid of a surgical bur) and/or the orientation of the surgical tool 16*a* relative to the tissue against which the working end is to be applied, and determines the location of the circulating tables 20, 22. In some embodiments, the navigation controller 46 forwards some of these data to a manipulator controller 74.

The navigation controller 46 also generates image signals that indicate the relative position of the surgical tool 16*a* to the tissue. These image signals are applied to the displays 24, 26. The displays 24, 26, based on these signals, generate images that allow the surgeon and staff to view the relative position of the surgical tool 16*a* to the surgical site. The displays, 24, 26, as discussed above, may include a touch screen or other input/output device that allows entry of commands.

The machine vision system 41 comprises one or more machine vision cameras 80 coupled to a machine vision controller 82. The machine vision controller 82 includes one or more processors, memory, and storage. The cameras 80 may be CCDs or CMOS sensor based cameras or other forms of machine vision camera. In some cases, the cameras 80 are arranged for stereoscopic operation, or single cameras combined with depth sensors, laser range finders, and the like, may be used. The machine vision controller 82 is coupled to the workflow controller WC, much like the navigation controller 46. In some embodiments, the machine vision controller 82 acts as the workflow controller WC or the machine vision controller 82 and the navigation controller 46 collectively act as the workflow controller WC.

Machine vision can identify and locate various objects in the operating room. The cameras 80 (and in some cases depth sensors) can be arranged to determine 3-D positions and/or orientations of the objects in a machine vision coordinate system MV of the machine vision system 41. In the embodiment shown, the cameras 80 are arranged in a housing/casing with the projectors 34, 36, 38 so that the projectors 34, 36, 38 can project visible light accurately in the same machine vision coordinate system MV (or other registered coordinate system as described below) by virtue of each projector 34, 36, 38 being calibrated to the machine vision coordinate system MV. The cameras 80 are arranged so that a field-of-view of the cameras 80 encompasses the objects in the operating room. As shown in FIG. 1, such objects may include the participants, the patient 12, the femur F and the tibia T of the patient 12, the manipulator 14, the surgical tools 16*a*, 16*b*, 16*c*, 16*d*, 16*e*, 16*f*, 16*g*, the implants 18*a*, 18*b*, 18*c*, 18*d*, the circulating tables 20, 22, and the like.

Initially, the objects to be located are viewed by the cameras 80 and identified. The objects may be identified by selecting the objects to be tracked using an input device I connected to the machine vision controller 82. The machine vision controller 82 may store detailed information regarding numerous objects in memory M on the machine vision controller 82 and the user may be able to manually select the objects to be tracked from a database of objects.

Additionally, or alternatively, the workflow controller WC may identify the objects to be tracked by the machine vision system 41 based on the pre-operative surgical plan. In this case, the workflow controller WC may have a preset list of workflow objects that are required for use in the pre-scripted surgical workflow and a list of contingent objects that could be required during the surgical procedure upon occurrence of a change event. The workflow controller WC may communicate these lists/identifications of the objects to the machine vision controller 82 so that the machine vision controller 82 acts to actively search for and locate the workflow objects as well as the contingent objects using machine vision software. For instance, object data (e.g., groups of pixels associated with different sizes and shapes of the various objects) may be stored in the machine vision controller 82. By selecting/identifying the objects to be located/tracked the machine vision software identifies the corresponding group of pixels and the machine vision software then operates to detect like groups of pixels using pattern recognition technology.

The machine vision controller 82 may comprise a frame grabber using either an analog or digital interface to obtain images of the operating room. Additionally, or alternatively, the cameras 80 may comprise digital cameras capable of direct connection to the machine vision controller 82. 2-D/3-D imaging, multispectral imaging, time-of-flight cameras and imaging, grid array based imaging, and/or stereoscopic vision/imaging, and the like may be employed.

After images are acquired by the cameras 80, they are processed. Multiple stages of processing may be used to extract the objects from the images (e.g., by comparing image data associated with the images to the object data stored in the machine vision controller 82). Machine vision image processing methods that may be employed include methods such as: stitching/registration; filtering; thresholding; pixel counting; segmentation; edge detection; color analysis; blob detection and extraction; pattern recognition/template matching; 2-D barcode reading; and/or optical character recognition; and/or any other suitable methods for processing images for purposes of machine vision identification, determining locations, and/or tracking one or more of the objects. Once the images are processed and the machine vision controller 82 identifies the objects to be tracked in the images, and hence in the machine vision coordinate system MV, then the control system can provide location information for the objects to the participants as needed, and/or can track movement of the objects.

The objects to be located/tracked can be identified using an interface in which one of the participants outlines or selects the objects to be tracked on the displays 24, 26. For instance, images taken by the cameras 80 from overhead the surgical site are displayed on the displays 24, 26 (and/or other displays). The participant then, using a mouse, digital pen, or the like, traces objects to be located/tracked on the display 24, 26. The machine vision software stores the pixels associated with the object that was traced into its memory.

The participant (or other user) identifies each object by a unique identifier such as naming the object using the machine vision software so that the saved group of pixels is now associated with the unique identifier. Multiple objects could be stored in this manner. The machine vision system 41 utilizes pattern recognition and associated software to later detect these objects.

The machine vision system 41 is able to detect movement of these objects by continuously taking images, reviewing the images, and detecting movement of the groups of pixels associated with the objects, or by any other suitable method of identifying and tracking the objects. In some cases, location information from the machine vision controller 82 of the machine vision system 41 for the objects can be transmitted to the workflow controller WC and/or the navigation controller 46. Likewise, location information from the navigation controller 46 can be transmitted from the navigation controller 46 to the machine vision controller 82.

The machine vision controller 82 may provide position information for the objects in the machine vision coordinate system MV. A tracker 85 (with passive or active markers or other tracking modality) is attached to the housing that supports the cameras 80 so that the camera unit 56 can track and thus register the position and orientation of the machine vision coordinate system MV relative to the localizer coordinate system LCLZ. Thus, location information from the machine vision system 41 can be determined in the localizer coordinate system LCLZ. Virtual boundaries can thus be associated with the objects in the machine vision system 41 and information relating to these virtual boundaries can be communicated to the workflow controller WC and/or the navigation controller 46.

The objects to be tracked by the machine vision system 41 can alternatively, or additionally be initially located and registered to the localizer coordinate system LCLZ using a navigation pointer P (see FIG. 1). For instance, the navigation pointer P has an integrated tracker and the navigation controller 46 stores initial data corresponding to a location of the tip of the pointer P relative to the tracker such that the navigation system 40 is able to locate and track the tip of the pointer P in the localizer coordinate system LCLZ. Accordingly, prior to the start of the surgical procedure, once all the objects are located in their desired locations, one of the participants may touch all of the objects with the pointer P, while identifying the objects in the navigation system 40 using one of the input devices I. So, for example, when the participant touches the surgical tool 16*b* with the tip of the pointer P, the participant may simultaneously trigger collection of that point in the localizer coordinate system LCLZ (via another input device I, such as a foot pedal). When the point is collected, the participant can also enter into the navigation software the identity of the object (via typing, pull-down selection from a list of objects, etc.).

Figure 1A:
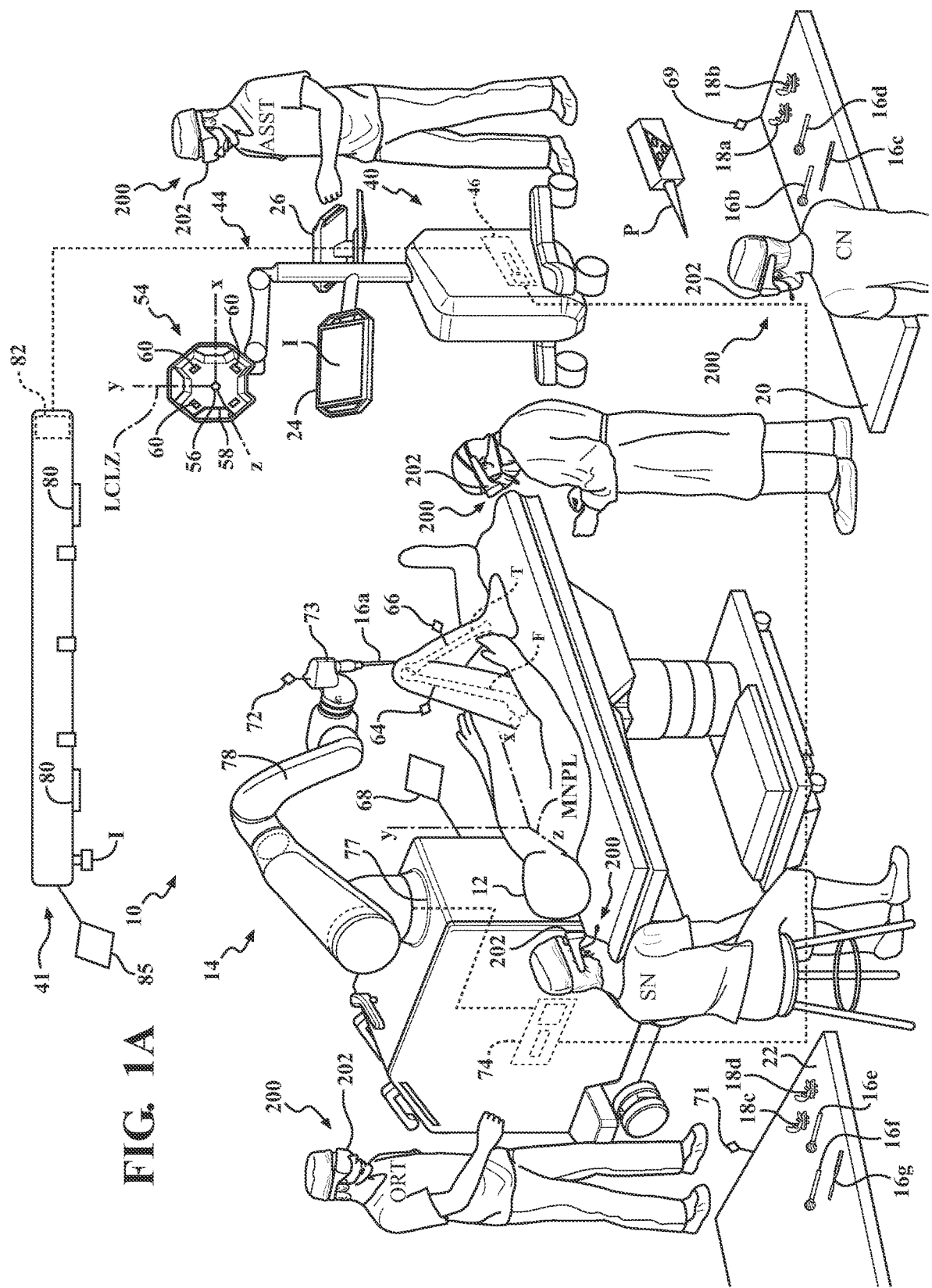
FIG. 1A is a perspective view of an operating environment illustrating various participants and alternative information conveyor devices for each of the participants.
Figure 2A:
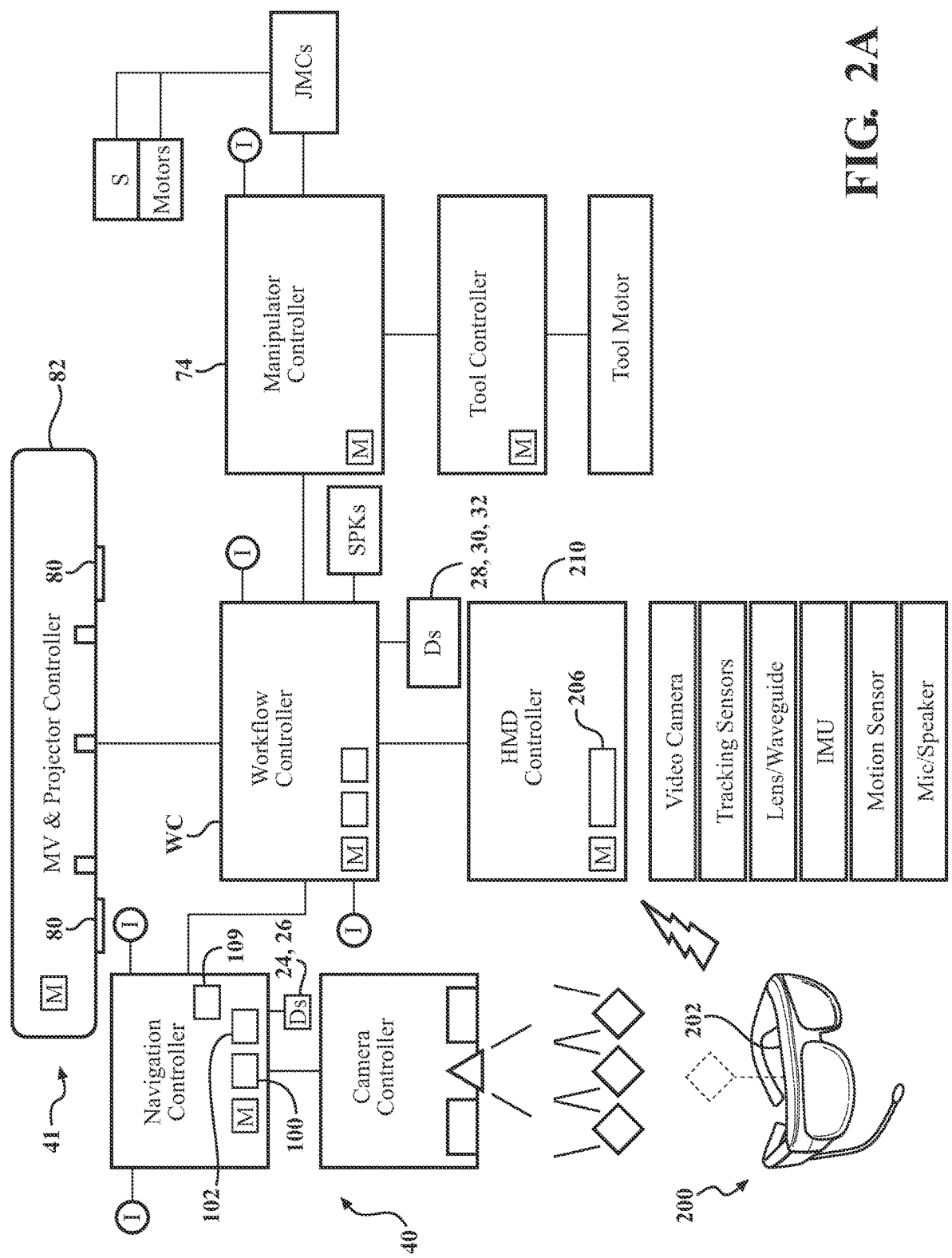
FIG. 2A is a schematic view of an alternative workflow control system.

Referring to FIGS. 1A and 2A, the head-mounted displays HMDs 200 may be employed in addition or as an alternative to one or more of the displays 24, 26, 28, 30, 32 to enhance visualization before, during, and/or after surgery. The HMD 200 can be used to visualize the same objects described as being visualized on the displays 24, 26, 28, 30, 32 and can also be used to visualize other objects, features, instructions, warnings, etc. The HMD 200 can be used to assist with locating the objects needed for the pre-scripted surgical workflow and the objects needed during change events. The HMD 200 can also be used to visualize instructions and/or warnings, among other uses, as described further below.

The HMD 200 may be a HoloLens® provided by Microsoft Corporation, which is referred to as a mixed reality HMD owing to its overlay of computer-generated images onto the real world (it should be appreciated that any reference to augmented reality encompasses mixed reality). Thus, in the embodiment described herein, the HMD provides a computational holographic display. Other types of mixed/augmented reality HMDs may also be used such as those that overlay computer-generated images onto video images of the real world. The HMD 200 may comprise a cathode ray tube display, liquid crystal display, liquid crystal on silicon display, or organic light-emitting diode display. The HMD 200 may comprise see-through techniques like that described herein comprising a diffractive waveguide, holographic waveguide, polarized waveguide, reflective waveguide, or switchable waveguide.

The HMD 200 comprises a head-mountable structure 202, which may be in the form of an eyeglass and may include additional headbands or supports to hold the HMD 200 on the user's head. In other embodiments, the HMD 200 may be integrated into a helmet or other structure worn on the user's head, neck, and/or shoulders.

The HMD 200 has visor and a lens/waveguide arrangement. The lens/waveguide arrangement is configured to be located in front of the user's eyes when the HMD is placed on the user's head. The waveguide transmits the computer-generated images to the user's eyes while at the same time, real images are seen through the waveguide (it being transparent) such that the user sees mixed reality (virtual and real).

An HMD controller 210 (see FIG. 2A) comprises an image generator 206 that generates the computer-generated images (also referred to as virtual images or holographic images) and that transmits those images to the user through the lens/waveguide arrangement. The HMD controller 210 controls the transmission of the computer-generated images to the lens/waveguide arrangement of the HMD 200. The HMD controller 210 may be a separate computer, located remotely from the support structure 202 of the HMD 200, or may be integrated into the support structure 202 of the HMD 200. The HMD controller 210 may be a laptop computer, desktop computer, microcontroller, or the like with memory, one or more processors (e.g., multi-core processors), input devices I, output devices (fixed display in addition to HMD 200), storage capability, etc.

The HMD 200 comprises a plurality of tracking sensors that are in communication with the HMD controller 210. In some cases, the tracking sensors are provided to establish a global coordinate system for the HMD 200, also referred to as an HMD coordinate system. The HMD coordinate system is established by these tracking sensors, which may comprise CMOS sensors or other sensor types, in some cases combined with IR depth sensors, to layout the space surrounding the HMD 200, such as using structure-from-motion techniques or the like. In one embodiment, four tracking sensors are employed.

The HMD 200 also comprises a photo/video camera in communication with the HMD controller 210. The camera may be used to obtain photographic or video images with the HMD 200, which can be useful in identifying objects or markers attached to objects, as will be described further below.

The HMD 200 further comprises an inertial measurement unit IMU in communication with the HMD controller 210. The IMU may comprise one or more 3-D accelerometers, 3-D gyroscopes, and the like to assist with determining a position and/or orientation of the HMD 200 in the HMD coordinate system or to assist with tracking relative to other coordinate systems. The HMD 200 may also comprise an infrared motion sensor to recognize gesture commands from the user. Other types of gesture sensors are also contemplated. The motion sensor may be arranged to project infrared light or other light in front of the HMD 200 so that the motion sensor is able to sense the user's hands, fingers, or other objects for purposes of determining the user's gesture command and controlling the HMD 200, HMD controller 210, workflow controller WC, navigation controller 46, machine vision controller 82, and/or manipulator controller 74 accordingly. Gesture commands can be used for any type of input used by the workflow system 10.

In order for the HMD 200 to be effectively used, the HMD 200 may be registered to the one or more of the objects used in the operating room. In one embodiment, the HMD coordinate system is a global coordinate system (e.g., a coordinate system of the fixed surroundings). In this case, a local coordinate system LOCAL (see FIG. 3) is associated with the HMD 200 to move with the HMD 200 so that the HMD 200 is always in a known position and orientation in the HMD coordinate system. The HMD 200 utilizes the four tracking sensors to map the surroundings and establish the HMD coordinate system. The HMD 200 then utilizes the camera to find objects in the HMD coordinate system. In some embodiments, the HMD 200 uses the camera to capture video images of markers attached to the objects and then determines the location of the markers in the local coordinate system LOCAL of the HMD 200 using motion tracking techniques and then converts (transforms) those coordinates to the HMD coordinate system. When these same markers or other markers in a known relationship thereto are located in the localizer coordinate system LCLZ, then the HMD coordinate system can be transformed to the localizer coordinate system LCLZ, as shown in FIG. 3.

In order to enhance the surgical procedure awareness of all the participants, the complete surgical team may wear HMDs 200, as shown in FIG. 1A. In some embodiments, such as those in which video cameras are integrated into the HMDs 200 to provide point of view (POV) video, through the POV video stream analysis or simpler context awareness mechanisms (e.g., sensory based feedback, heuristics based on inputs from isolated sensors, etc.), a computer-based model of the surgical context can provide participant specific mixed/augmented reality aids to facilitate the current task being performed by the individual participant or help prepare for their next contribution to the pre-scripted surgical workflow or change event.

In lieu of a computer based model, a human-based feed of mixed/augmented reality aids that are superimposed onto the participants' own POVs can be accomplished through a surgical workflow supervisor that simultaneously oversees individual actions on a master display (e.g., fed by one or more of the video cameras in the operating room, such as the cameras 80 or video cameras in the same housing as the cameras 80) and coordinates participants' interactions in order to ensure an uninterrupted flow of surgery. Such a surgical workflow supervisor could be used in other embodiments not employing the HMDs 200 as well, but instead controlling the displays 24, 26, 28, 30, 32 and/or the projectors 34, 36, 38 or other information conveyor devices to feed such devices with graphical or textual information specific to each participant, such as described further below.

In one embodiment, two or more participants and their HMDs 200 can be linked together in conjunction with the contextual information of the pre-scripted surgical workflow or change events. The participants may be linked by sharing their current POV or in a more inherent way, by sharing the objects of interest being addressed at any given point in time by any of the participants. Within this embodiment, a first participant is able to enhance his or her personal assessment of a second participant's circumstances through the display of mixed/augmented reality aids as the first participant directs his/her personal POV to that of the second participant. As the first participant realizes an opportunity for event flow optimization or foresees an impending interaction to maintain the flow of events, appropriate interplay with the different participants or surgical environment can take place. This interaction can be directly executed by the first participant or can be facilitated through mixed/augmented reality aids or other computer-assisted aids, which in turn can be automatically generated or created by the first participant to support the second participant's course of actions.

In some versions, the surgical tool 16a forms part of the end effector of the manipulator 14. In some versions, the manipulator 14 is absent. The manipulator 14 has a base 77, a plurality of links 78 extending from the base 77, and a plurality of active joints (not numbered) for moving the surgical tool 16a with respect to the base 77. The manipulator 14 has the ability to operate in a manual mode or a semi-autonomous mode in which the surgical tool 16a is moved along a predefined tool path, as described in U.S. Pat. No. 9,119,655, entitled, "Surgical Manipulator Capable of Controlling a Surgical Instrument in Multiple Modes," the disclosure of which is hereby incorporated by reference, or the manipulator 14 may be configured to move in the manner described in U.S. Pat. No. 8,010,180, hereby incorporated by reference.

The manipulator controller 74 can use the position and orientation data of the surgical tool 16a and the patient's anatomy to control the manipulator 14 as described in U.S. Pat. No. 9,119,655, entitled, "Surgical Manipulator Capable of Controlling a Surgical Instrument in Multiple Modes," the disclosure of which is hereby incorporated by reference, or to control the manipulator 14 as described in U.S. Pat. No. 8,010,180, hereby incorporated by reference.

The manipulator controller 74 may have a central processing unit (CPU) and/or other manipulator processors, memory (not shown), and storage (not shown). The manipulator controller 74, also referred to as a manipulator computer, is loaded with software as described below. The manipulator processors could include one or more processors to control operation of the manipulator 14. The processors can be any type of microprocessor or multi-processor system. The term processor is not intended to limit any embodiment to a single processor.

A plurality of position sensors S are associated with the plurality of links 78 of the manipulator 14. In one embodiment, the position sensors S are encoders. The position sensors S may be any suitable type of encoder, such as rotary encoders. Each position sensor S is associated with a joint actuator, such as a joint motor M. Each position sensor S is a sensor that monitors the angular position of one of six motor driven links 78 of the manipulator 14 with which the position sensor S is associated. Multiple position sensors S may be associated with each joint of the manipulator 14 in some embodiments. The manipulator 14 may be in the form of a conventional robot or other conventional machining apparatus, and thus the components thereof shall not be described in detail.

In some modes, the manipulator controller 74 determines the desired location to which the surgical tool 16a should be moved. Based on this determination, and information relating to the current location (e.g., pose) of the surgical tool 16a, the manipulator controller 74 determines the extent to which each of the plurality of links 78 needs to be moved in order to reposition the surgical tool 16a from the current location to the desired location. The data regarding where the plurality of links 78 are to be positioned is forwarded to joint motor controllers JMCs that control the joints of the manipulator 14 to move the plurality of links 78 and thereby move the surgical tool 16a from the current location to the desired location. In other modes, the manipulator 14 is capable of being manipulated as described in U.S. Pat. No. 8,010,180, hereby incorporated by reference, in which case the actuators are controlled by the manipulator controller 74 to provide gravity compensation to prevent the surgical tool 16a from lowering due to gravity and/or to activate in response to a user attempting to place the working end of the surgical tool 16a beyond a virtual boundary.

Referring to FIG. 3, tracking of objects is generally conducted with reference to the localizer coordinate system LCLZ. The localizer coordinate system LCLZ has an origin and an orientation (a set of x, y, and z axes). During the procedure one goal may be to keep the localizer coordinate system LCLZ in a known position. Each tracker 64, 66, 68, 69, 71, 72, 85 and object being tracked also has its own coordinate system separate from the localizer coordinate system LCLZ. For example, the bone trackers 64, 66 (only one of which is shown in FIG. 3) and the base tracker 68 have their own coordinate systems represented in FIG. 3, respectively, as bone tracker coordinate systems BTRK1, BTRK2 (only BTRK1 shown), and base tracker coordinate system BATR.

Navigation system 40 can monitor the positions of one or more of the objects being tracked by monitoring the positions of the trackers that are attached (e.g., fixed) to the objects and via data that associates the trackers with the objects, such as registration data, calibration data, and the like. The description below sets forth in detail how the navigation system 40 operates to monitor the position of the surgical tool 16a relative to the femur F and tibia T of the patient by monitoring the positions of trackers 64, 66, 68 (or 72) and from sensor data. The locations of the other objects, such as the surgical tools 16b-16g, implants 18a-18d, the circulating tables 20, 22, the machine vision system 41, and the like can be determined using the same techniques and methodology described below. Additionally, all of the objects can be tracked in the same coordinate system (e.g., a common coordinate system) or in different coordinate systems if desired.

Prior to the start of the procedure, pre-operative images of the femur F and tibia T are generated (or of other tissues in other embodiments). These images may be based on MRI scans, radiological scans or computed tomography (CT) scans of the patient's anatomy. These images or three-dimensional models developed from these images are mapped to a femur coordinate system FBONE and tibia coordinate system TBONE using well known methods (see transform T11). One of these models is shown in FIG. 3 with model coordinate system MODEL2. These images/models are fixed in the femur coordinate system FB ONE and tibia coordinate system TBONE. As an alternative to taking pre-operative images, plans for treatment can be developed in the operating room from kinematic studies, bone tracing, and other methods. The models described herein may be represented by mesh surfaces, constructive solid geometry (CSG), voxels, or using other model constructs.

During an initial phase of the procedure, the bone trackers 64, 66 are firmly affixed to the bones of the patient. The pose (position and orientation) of coordinate systems FBONE and TBONE are mapped to coordinate systems BTRK1 and BTRK2, respectively (see transform T5). In one embodiment, the navigation pointer P, such as disclosed in U.S. Pat. No. 7,725,162 to Malackowski, et al., hereby incorporated by reference, having its own tracker, may be used to register the femur coordinate system FBONE and tibia coordinate system TBONE to the bone tracker coordinate systems BTRK1 and BTRK2, respectively. Given the fixed relationship between the bones and their bone trackers 64, 66, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 64, 66. These pose-describing data are stored in memory integral with both manipulator controller 74 and navigation controller 46.

The working end of the surgical tool 16a has its own coordinate system. In some embodiments, the surgical tool 16a comprises an accessory that is removably coupled to the surgical tool 73. The accessory may be referred to as the energy applicator and may comprise a bur, an electrosurgical tip, an ultrasonic tip, or the like. The coordinate system of the surgical tool 16a is referenced herein as coordinate system EAPP. The origin of the coordinate system EAPP may represent a centroid of a surgical cutting bur, for example. In other embodiments, the accessory may simply comprise a probe or other surgical tool with the origin of the coordinate system EAPP being a tip of the probe. The pose of coordinate system EAPP is registered to the pose of base tracker coordinate system BATR before the procedure begins (see transforms T1, T2, T3). Accordingly, the poses of these coordinate systems EAPP, BATR relative to each other are determined. The pose-describing data are stored in memory integral with both manipulator controller 74 and navigation controller 46.

In order to determine the current location of the surgical tool 16a (e.g., its TCP), data from the position sensors S (e.g., rotary encoders) is used to determine measured joint angles. The measured joint angles of the joints are forwarded to a forward kinematics module (not shown). Based on the measured joint angles and preloaded data, the forward kinematics module determines the pose of the surgical tool 16a in the manipulator coordinate system MNPL (see transform T3 in FIG. 3). The preloaded data are data that define the geometry of the plurality of links 78 and joints. With this sensor data, the manipulator controller 74 and/or navigation controller 46 can transform coordinates from the localizer coordinate system LCLZ into the manipulator coordinate system MNPL, vice versa, or can transform coordinates from one coordinate system into any other coordinate system described herein using conventional transformation techniques. In many cases, the coordinates of interest associated with the surgical tool 16a (e.g., the tool center point or TCP), the virtual boundaries, and the tissue being treated, are transformed into the common coordinate system for purposes of relative tracking and display.

In the embodiment shown in FIG. 3, transforms are utilized to transform all relevant coordinates into the femur coordinate system FBONE so that the position and/or orientation of the surgical tool 16a can be tracked relative to the position and orientation of the femur (e.g., the femur model) and/or the position and orientation of the volume of material to be treated by the surgical tool 16a (e.g., a cut-volume model: see transform T10). The relative positions and/or orientations of these objects can also be represented on the displays 24, 26, 28, 30, 32 to enhance the participant's visualization before, during, and/or after surgery.

In some embodiments, a separate HMD tracker 218, similar to the trackers 64, 66, 68, 69, 71, 72, 85 could be mounted to the HMD 200 (e.g., fixed to the support structure 202). The HMD tracker 218 would have its own HMD tracker coordinate system HMDTRK that is in a known position/orientation relative to the local coordinate system LOCAL or could be calibrated to the local coordinate system LOCAL using conventional calibration techniques. In this embodiment, the local coordinate system LOCAL becomes the HMD coordinate system and the transforms T7 and T8 would instead originate therefrom. The localizer 54 could then be used to track movement of the HMD 200 via the HMD tracker 218 and transformations could then be calculated to transform coordinates in the local coordinate system LOCAL to the localizer coordinate system LCLZ, the femur coordinate system FBONE, the manipulator coordinate system MNPL, or other coordinate system.

A localization engine 100 (see FIG. 2) is a software module that can be considered part of the navigation system 40. Components of the localization engine 100 run on navigation controller 46. In some embodiments, the localization engine 100 may run on the manipulator controller 74.

Localization engine 100 receives as inputs the optically-based signals from the camera controller 62 and, in some embodiments, non-optically based signals from a tracker controller. Based on these signals, localization engine 100 determines the pose of the bone tracker coordinate systems BTRK1 and BTRK2 in the localizer coordinate system LCLZ (see transform T6). Based on the same signals received for the base tracker 48, the localization engine 100 determines the pose of the base tracker coordinate system BATR in the localizer coordinate system LCLZ (see transform T1). The localization engine 100 can also determine the pose of the other tracker coordinate systems in any desired coordinate system, including the localizer coordinate system LCLZ.

The localization engine 100 forwards the signals representative of the poses of trackers 64, 66, 68 (and/or other trackers) to a coordinate transformer 102. Coordinate transformer 102 is a navigation system software module that runs on navigation controller 46. Coordinate transformer 102 references the data that defines the relationship between the pre-operative images of the patient and the bone trackers 64, 66. Coordinate transformer 102 also stores the data indicating the pose of the working end of the surgical tool 16a relative to the base tracker 48, such as the sensor data previously described, and/or other data, such as geometric data indicating the pose of the other trackers relative to their associated objects that are being tracked.

During the procedure, the coordinate transformer 102 receives the data indicating the relative poses of the trackers 64, 66, 68 (and/or other trackers) to the localizer 54. Based on these data, the previously loaded data, and the above-described sensor data from the manipulator 14, the coordinate transformer 102 generates data indicating the relative positions and orientations of the coordinate system EAPP and the bone coordinate systems, FBONE and TBONE, and/or other object coordinate systems.

As a result, coordinate transformer 102 generates data indicating the position and orientation of the working end of the surgical tool 16a relative to the tissue (e.g., bone) against which the working end is applied, and/or poses of any of the other tracked objects in the desired coordinate system. Image signals representative of these data are forwarded to displays 24, 26 (and/or other displays) enabling the surgeon and staff to view this information. In certain embodiments, other signals representative of these data can be forwarded to the manipulator controller 74 to guide the manipulator 14 and corresponding movement of the surgical tool 16a.

Figure 4:
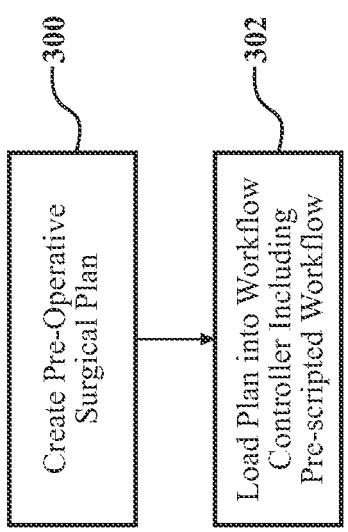
FIG. 4 illustrates steps of creating a pre-operative surgical plan and loading the plan into a workflow controller.

Referring to FIG. 4, the initial steps performed by the workflow system 10 are shown, including creating the pre-operative surgical plan in step 300 and loading the pre-operative surgical plan into the workflow controller WC in step 302, including the pre-scripted workflow (and associated workflow steps). Pre-operative surgical plans are prescribed by surgeons for each patient and describe in detail the type of procedure being performed, the target anatomy that is being treated, the types, sizes, and/or shapes of implants (if any) that are being implanted, the tools required for the surgery, surgeon preferences, and other information.

Creation of the pre-operative surgical plan includes several steps. First, the patient is diagnosed to determine the appropriate treatment for the patient. Next, the surgeon prescribes the treatment. In the embodiment shown, the treatment is a total knee replacement, but other forms of treatment/intervention are possible. The surgeon's prescription includes the imaging of the patient's bones, i.e., the femur and tibia using MRI, CT scan, etc. Once imaging of the bones is complete, the images are used to prepare or select an appropriate design of a total knee implant. The design includes the type of implant, the size/shape of the implant, and the location on the bones to which the implant is to be fixed (which includes identifying the tissue to be removed to receive the implant). The tools needed to prepare the patient to receive the implant may also be determined. This information may be stored in electronic form in a computer readable format such as a text file, image file, or the like. The design may be prepared or selected by the surgeon or by a third party. Once the design of the knee implant is determined, the surgeon reviews the design, and if acceptable, approves the design and the surgical procedure is scheduled. Once the surgical procedure is scheduled, the operating room is prepared for the surgery, which includes arranging the objects based on the pre-operative surgical plan.

The pre-operative surgical plan is stored in memory M in the navigation controller 46. The pre-operative surgical plan may be stored using a wired or wireless internet connection to the navigation controller 46, by flash memory device, or the like. In some cases, the surgeon SU or his or her designee transfers the encrypted pre-operative surgical plan (including design information) to the navigation system 40, via hospital or surgical center secure local area network (Ethernet), secure USB flash drive, or secure wireless (WiFi) connection. In some embodiments, the pre-operative surgical plan is created using the navigation system 40.

Figure 5:
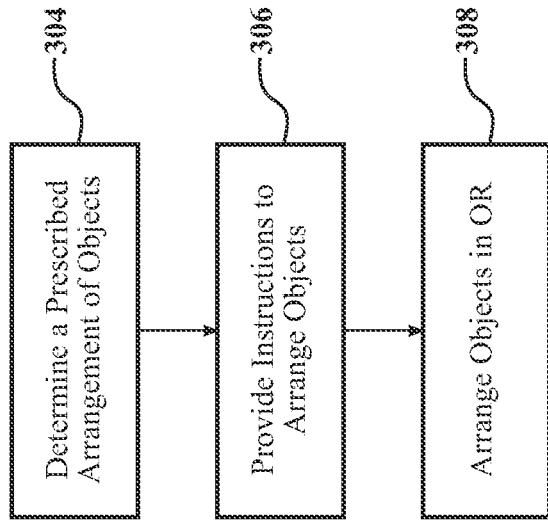
FIG. 5 illustrates steps associated with arranging surgical objects in the operating room.

Referring to FIG. 5, once the surgical procedure information (e.g., information from the pre-operative surgical plan) is stored in the navigation controller 46, an OR Setup module 109 (see FIG. 2) can be used to begin setting up the objects in the operating room. The OR Setup module 109 is a software module that runs on navigation controller 46 and/or workflow controller WC. The participants can operate the OR Setup module 109 using the user interface and displays 24, 26 of the navigation system 40.

The OR Setup module 109 determines a prescribed arrangement of objects in step 304 based on the surgical procedure information, which is input into the OR Setup module 109. The prescribed arrangement of objects can be determined by looking for certain information loaded into the OR Setup module 109 (e.g., from the pre-operative surgical plan) and matching the information to one of a plurality of prescribed arrangements listed in a look-up table/database. The look-up table/database is stored on the navigation controller 46. For instance, the information loaded may identify the type of procedure as "TOTAL KNEE-LEFT". The OR Setup module 109 is programmed to select a prescribed arrangement of objects based on this type of procedure by finding in the look-up table the specific arrangement associated with "TOTAL KNEE-LEFT".

Prescribed arrangements of the various objects to be placed in the operating room may include overhead object layout plans. The overhead layout plans may be stored in the navigation controller 46 as image files or other file types. Alternatively, the overhead layout plans may be part of the pre-operative surgical plan and/or loaded along with the surgical procedure information into the OR Setup module 109. Different layout plans may be associated with different procedure types. Different layout plans may also be associated with different surgeon preferences.

Once the prescribed arrangement of the various objects is determined, the navigation system 40 provides instructions to arrange the objects accordingly in step 306. Such instructions can be carried out by one or more of the participants or other personnel in step 308. Other details regarding the prescribed arrangement of the objects and the instructions on arranging the objects are disclosed in U.S. Patent Application Pub. No. 2014/0276855, which is hereby incorporated herein by reference.

Figure 6:
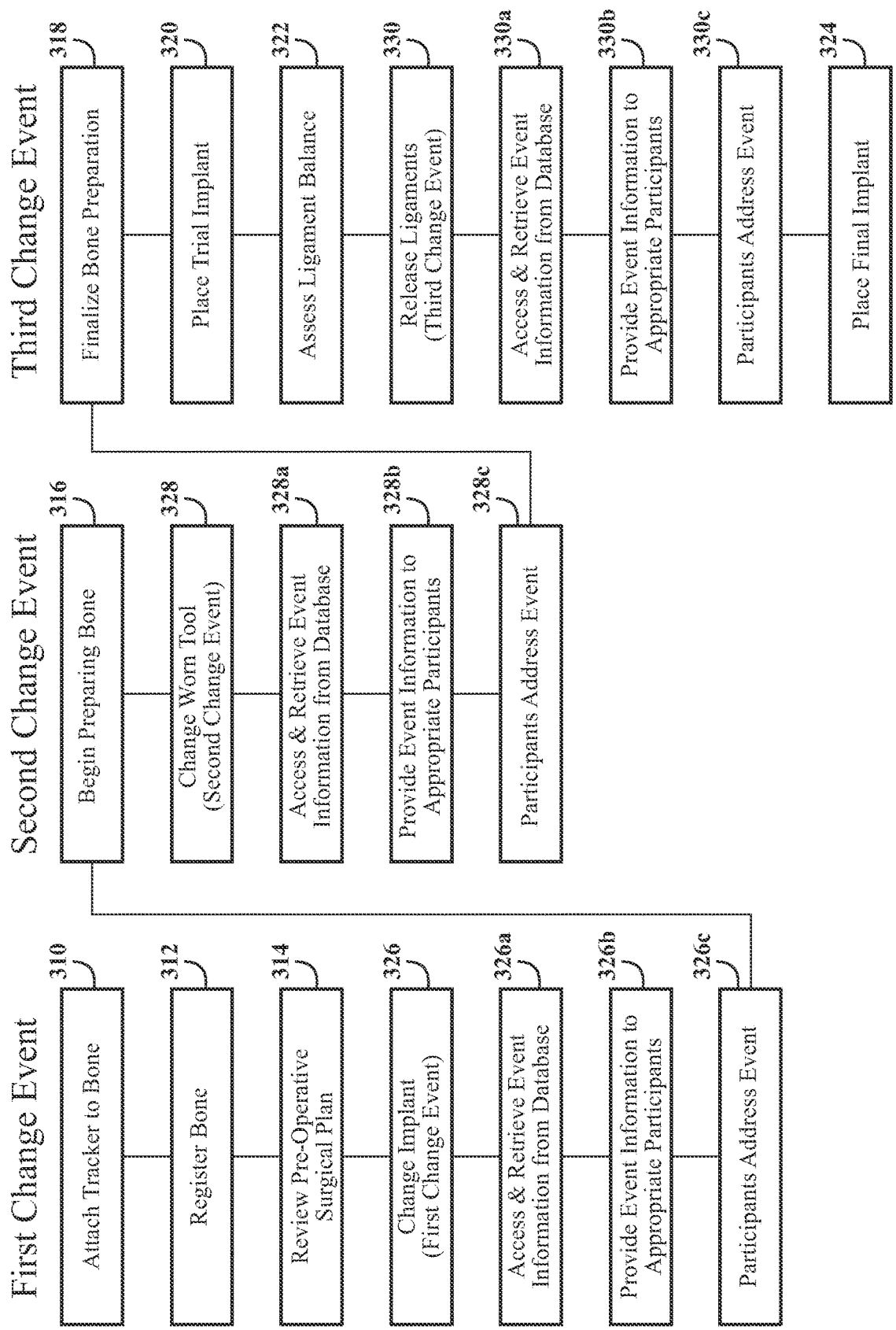
FIG. 6 illustrates examples of a pre-scripted surgical workflow with change events that deviate from the pre-scripted surgical workflow.

Referring to FIG. 6, workflow steps from a sample pre-scripted surgical workflow for a total knee replacement procedure are shown as steps 310-324. Steps associated with change events are also illustrated. In FIG. 6, three change events are illustrated, i.e., when the participants are required to deviate from the pre-scripted workflow. The first change event 326 is associated with the surgeon SU determining that a different size implant is required to be installed on the patient. This could occur in response to the surgeon SU determining that certain anatomical considerations not shown on the pre-operative images require a different implant, such as may be revealed when exposing the patient's real bone. The second change event 328 results from the surgical tool 16a becoming worn. In one embodiment, surgical burs may be used that become worn as bone is removed, thereby requiring a new bur. The third change event 330 occurs as a result of ligament balancing performed by the surgeon SU. Here, the assessment of ligament balancing results in the surgeon determining that one or more ligaments need to be released.

The workflow system 10 operates to identify the change events 326, 328, 330 by various methods. For instance, the pre-scripted surgical workflow, when determined, may also have a list of possible change events associated with it. Accordingly, the workflow controller WC may provide on the displays 24, 26 or other displays 28, 30, 32, the ability for the surgeon SU or other participants to select the change event from a drop down list or other menu. In other versions, the workflow system 10 may automatically determine that a change event is occurring based on other inputs into the software by the surgeon SU or other participants. For instance, the first change event 326 relates to the surgeon SU selecting a different implant from that prescribed in the pre-operative surgical plan. The intraoperative planning software may provide the surgeon SU with the ability to check the pre-operative placement of the implant originally selected, and the ability to either shift placement of the implant relative to the patient's anatomy or to choose a different size of implant. If the surgeon SU chooses a different size of implant, then the workflow controller WC is advised of the new selection, via user input on the user interface, via automatic detection, or the like, and automatically responds to the change event as discussed further below.

In some cases, the workflow system 10 has the ability to predict when a change event may occur and respond automatically. For instance, the second change event 328 relates to the surgical tool 16a becoming worn and requiring replacement. This change event can be based on the time of operation of the surgical tool 16a, the rotational speed of the surgical tool 16a during use, and forces/torques acting upon the surgical tool 16a during use, all of which can be measured by the tool controller and/or manipulator controller 74 via sensors, such as force/torque sensors, speed sensors, current sensors, and the like. Wear could also be determined based on current in the motor driving the surgical tool 16a, temperature of the surgical tool 16a (measured by temperature sensors connected to the tool controller and coupled to the workflow controller), as well as collisions detected with ancillary instrumentation. The wear of the surgical tool 16a can be determined/predicted based on such factors and the workflow system 16a can therefore determine/predict when the surgical tool 16a is worn or will be worn and initiate the second change event 328 automatically.

Once a change event is identified, then the surgical team deviates from the pre-scripted workflow to address the change event. The workflow system 10 continues by first accessing and retrieving the change event information associated with the change event from the database in steps 326a, 328a, 330a. In steps 326b, 328b, 330b, the workflow system 10 provides change event information to the appropriate participants. This may include providing different information to the different participants. In some cases, first information may be provided to a first group of the participants and second information may be provided to a second group of the participants. In other cases, different information is provided to each of the participants and is tailored to the responsibilities/duties of each of the participants associated with the particular change event. In steps 326c, 328c, 330c, the participants address the change event.

Figure 7:
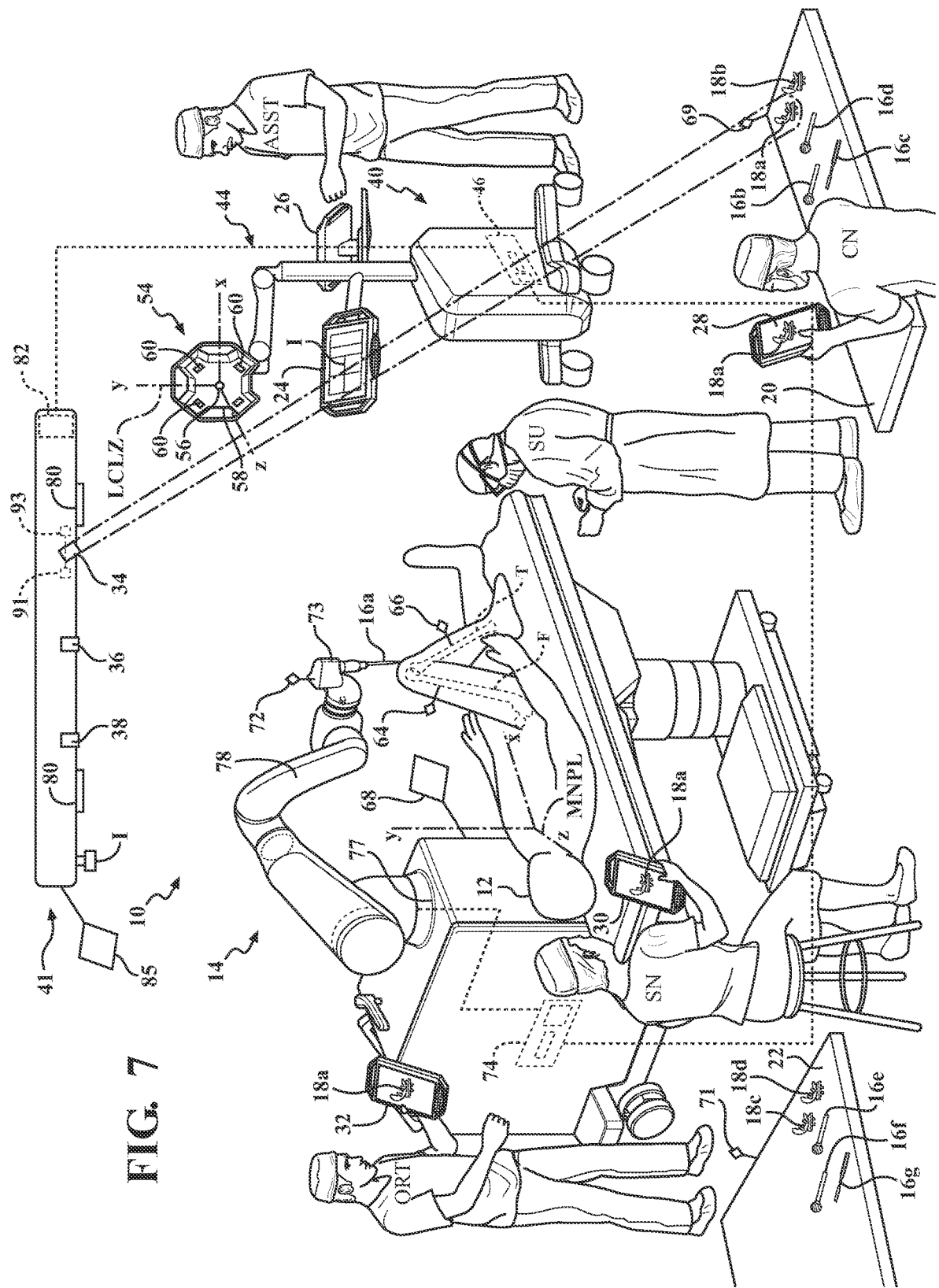
FIGS. 7, 9, and 11 illustrate examples of how the workflow control system provides event information associated with change events.
Figure 8:
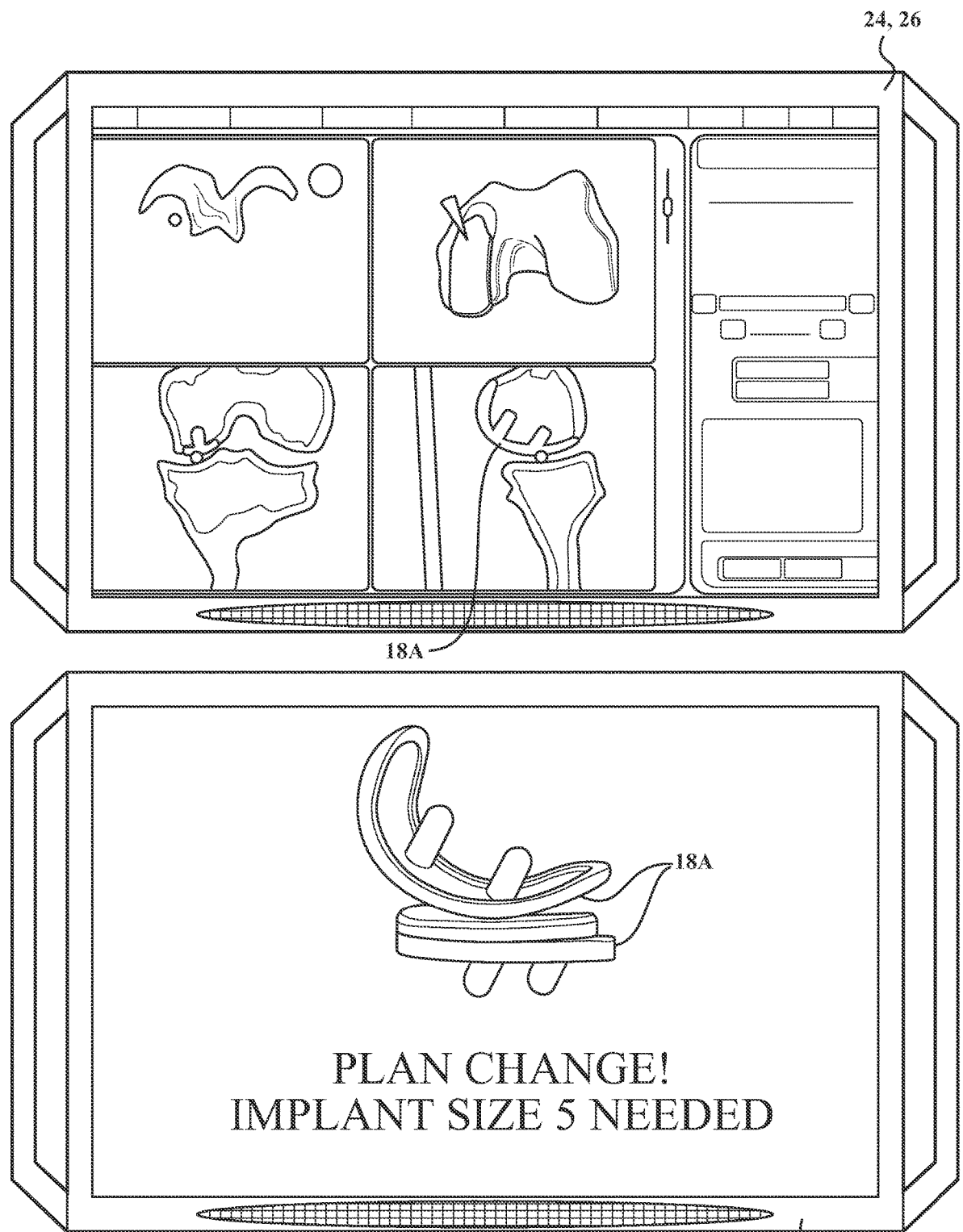
FIGS. 8, 10, and 12 illustrate displays of different participants to illustrate the different event information received by the different participants in response to change events.

FIGS. 7 and 8 illustrate one example of different event information being provided to the participants in step 326b. When the surgeon selects a different implant for the surgical procedure, the workflow system 10 acts to provide the surgeon SU and the assistant ASST with first event information, which includes allowing the surgeon SU to plan the placement of the new implant on a virtual 3-D model of the patient's anatomy, such as by prompting the surgeon SU on the displays 24, 26, or elsewhere, to place a virtual representation of the implant onto the virtual 3-D model of the patient's anatomy via a user interface, e.g., a touch screen. This may comprise adjusting a location of the virtual implant on display via input from the surgeon, e.g., via toggle buttons, finger swiping, and the like, that are employed to move the 3-D representation of the virtual implant relative to the 3-D model of the patient's anatomy in one or more degrees of freedom until the virtual implant is in a desired location relative to the 3-D model. This location can then be saved by the workflow controller and/or other controller for later use. The workflow system 10 provides the scrub nurse SN, the circulating nurse CN, and the operating room technician ORT with different, second event information, which includes an identity of the new implant selected by the surgeon SN, and the location of the new implant if the new implant was originally laid out in the operating room during the arrangement of the objects. In many cases, several implant sizes/types are made available in the operating room in anticipation of such change events.

As shown in FIG. 8, in one example, the workflow controller WC causes the first event information to be shown on the displays 24, 26 to the surgeon SU and the assistant ASST, and causes the second event information to be shown on the displays 28, 30, 32 to the scrub nurse SN, the circulating nurse CN, and the operating room technician ORT. Additionally, referring to FIG. 7, the workflow system 10, via the workflow controller WC operates one of the projectors 34, 36, 38 to direct visible light onto the new implant 18a sitting on the circulating table 20.

The projectors 34, 36, 38 may be coupled to motorized drive systems to move in response to commands from the workflow controller WC so that the visible light is directed to the appropriate location. Such drive systems may comprise a set of motors 91, 93 (see FIG. 7) to move the projectors 34, 36, 38 in two of more degrees of freedom to enable the visible light to be directed from the projector 34, 36, and/or 38 to the new implant 18a. For instance, as shown in FIG. 7, motors 91, 93 may change an orientation of the projector (in pitch and/or yaw) to be directed toward the new implant 18a. The workflow controller WC determines the amount to reorient the projector 34, 36, 38 based on the known position of the new implant 18a in the localizer coordinate system LCLZ and the current position and orientation of the projector 34, 36, 38 in the localizer coordinate system LCLZ. The various implants may be located/tracked via the navigation system 40 (e.g., via their own tracker fixed thereto) and/or via the machine vision system 41, and/or via other suitable location/tracking methods.

The current position of the projector 34, 36, 38 (which may be a position of an origin of a projector coordinate system) may be fixed to housing 97 and known from prior calibration and stored in the memory M of a projector controller (which may also be the machine vision controller 82). In some cases, the position of the origin remains fixed as the projector is reoriented in pitch/yaw (e.g., the origin is located at a central pivot about which the pitch/yaw of the projector 34, 36, 38 is adjusted. The current orientation can be detected by one or more sensors S that detect the pitch/yaw of the projector 34, 36, 38, such as sensors S on the motors 91, 93, or other sensors capable of detecting pitch/yaw positions of the projector (e.g., hall-effect sensors, potentiometers, inertial sensors, etc.). From the known position of the projector 34, 36, 38 (e.g., the origin) and the known position of the new implant 18a (e.g., initially determined using the navigation pointer P), a trajectory from the projector 34, 36, 38 to the new implant 18a can be calculated. The orientation of the projector 34, 36, 38 can then be changed by the projector controller via the motors 91, 93 to align with the trajectory. The projector 34, 36, 38 may then be controlled to project the visible light continuously or to flash the visible light onto the new implant 18a to indicate the location of the new implant 18a to the surgical team.

In some embodiments, the circulating table 20 may be outfitted with one or more light sources, such as LEDs that the workflow controller WC illuminates to indicate to the circulating nurse CN and the scrub nurse SN that the new implant 18a located on the circulating table 20 needs to be readied for implantation (e.g., removed from a sterile package, handed from the circulating nurse CN to the scrub nurse, etc.).

Figure 9:
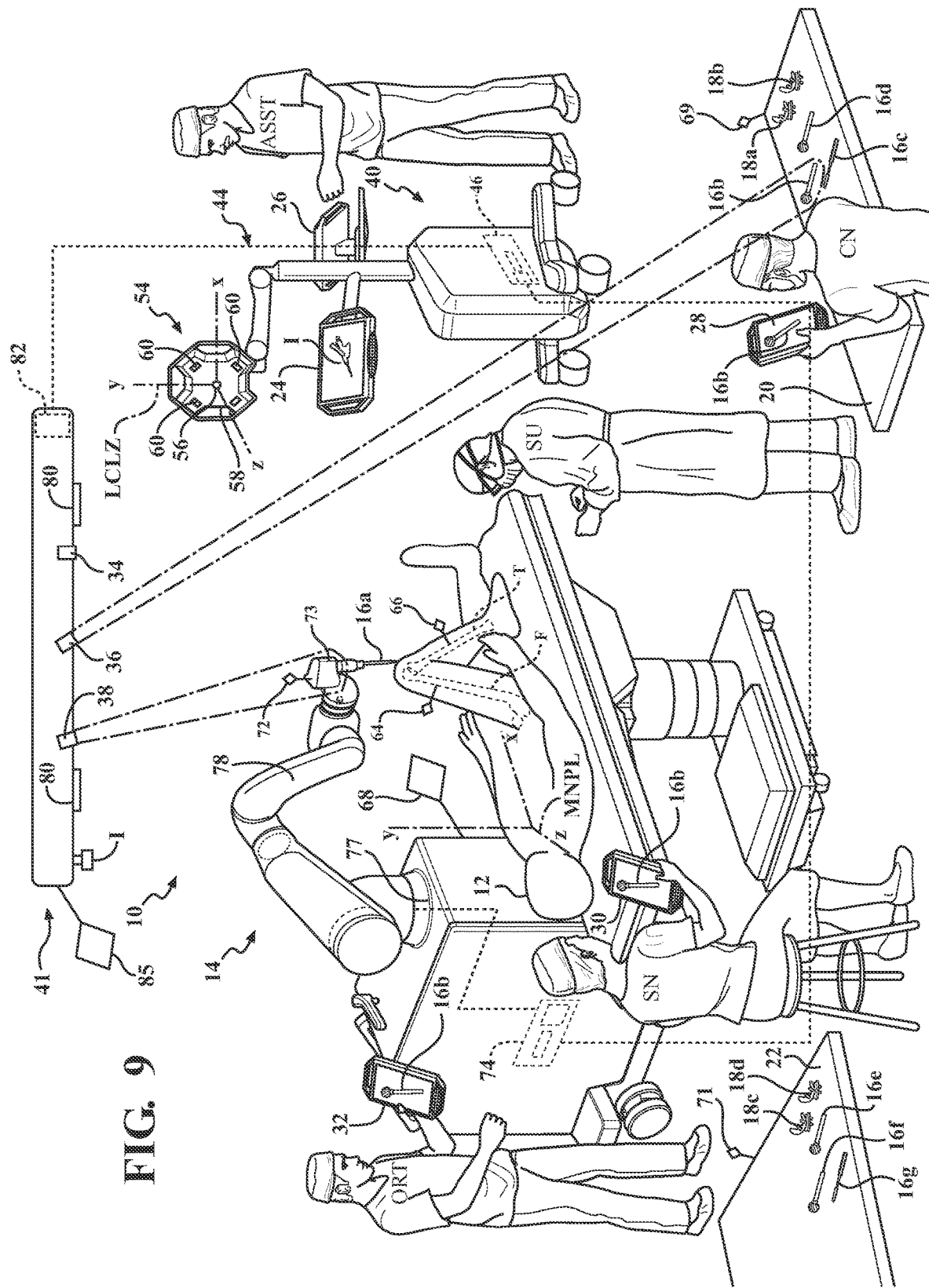
Figure 10:
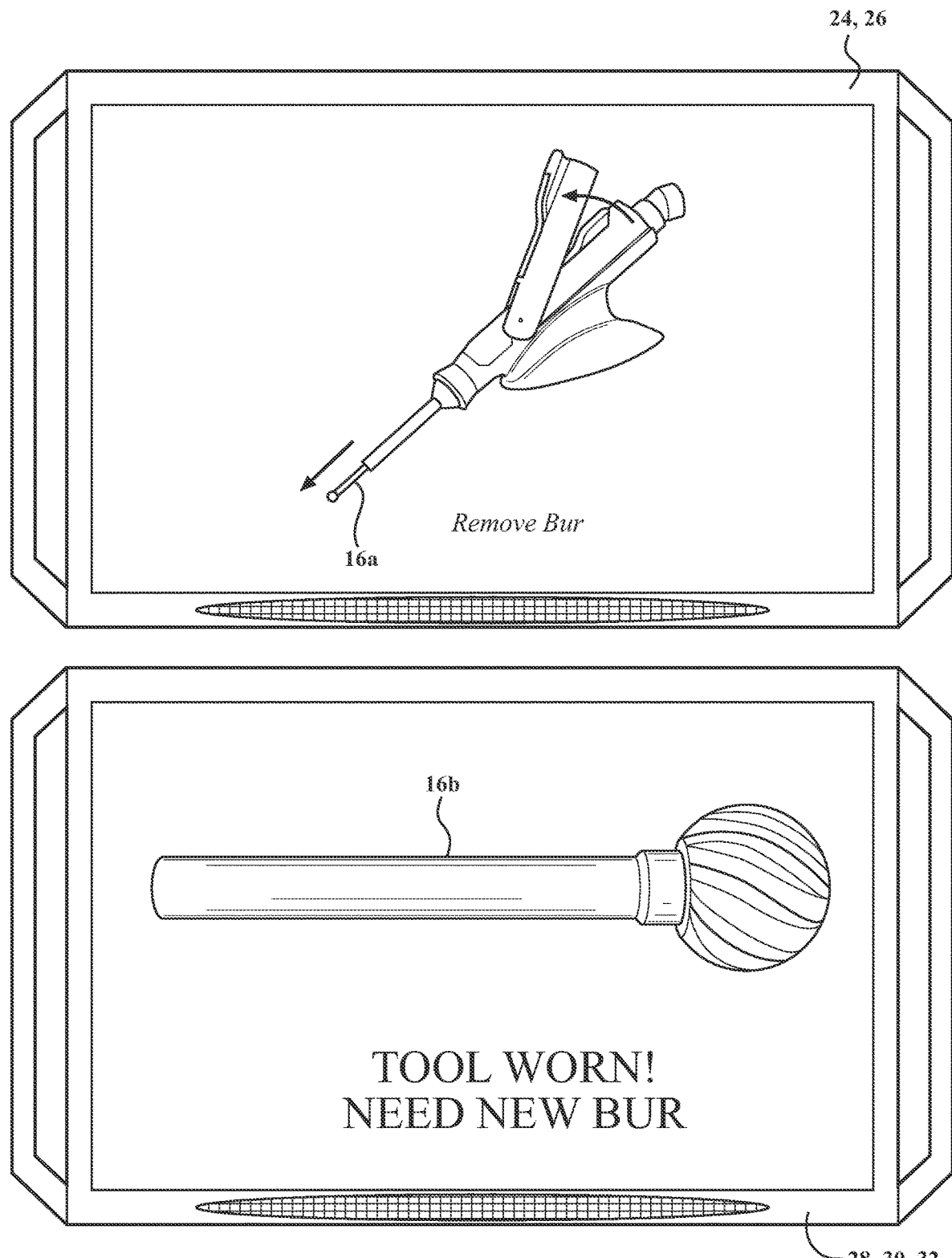

FIGS. 9 and 10 illustrate another example of different event information being provided to the participants in step 328b. When the workflow system 10 determines that the surgical tool 16a is worn and a new surgical tool 16b needs to be installed on the manipulator 14, the workflow system 10 acts to provide the surgeon SU and the assistant ASST with first event information, which includes instructing the surgeon SU as to how to remove the old surgical tool 16a and replace it with the new surgical tool 16b. The workflow system 10 provides the scrub nurse SN, the circulating nurse CN, and the OR technician ORT with different, second event information, which includes an identity of the new surgical tool 16b and the location of the new surgical tool 16b, which can be determined when the new surgical tool 16b was originally laid out in the operating room during the arrangement of the objects. In many cases, new surgical tools 16b are made available in the operating room in anticipation of such change events. The various surgical tools may be located/tracked via the navigation system 40 (e.g., via their own tracker fixed thereto or via the navigation pointer P) and/or via the machine vision system 41, and/or via other suitable location/tracking methods.

As shown in FIG. 10, the workflow controller WC causes the first event information to be shown on the displays 24, 26 to the surgeon SU and the assistant ASST, and causes the second event information to be shown on the displays 28, 30, 32 to the scrub nurse SN, the circulating nurse CN, and the OR technician ORT. Additionally, the workflow system 10, via the workflow controller WC and the projector controller coupled thereto, operates two of the projectors 34, 36, 38 in the manner described above to direct visible light onto the old surgical tool 16a requiring replacement and the new surgical tool 16b sitting on the circulating table 20.

In some embodiments, the circulating table 20 may be outfitted with one or more light sources, such as LEDs that the workflow controller WC illuminates to indicate to the circulating nurse CN and the scrub nurse SN that the new surgical tool 16b needs to be readied for use (e.g., removed from a sterile package, handed from the circulating nurse CN to the scrub nurse SN, etc.). Additionally, the markers (e.g., active LEDs) on the tool tracker 72 may be activated by the workflow controller WC to be illuminated at the same time, flashed, etc., to indicate to the surgeon SU that the tool 16a needs to be replaced.

The workflow system 10 determines that the surgical tool 16a being used for bone removal is no longer delivering optimal results and needs to be replaced. In this case, the workflow system 10 will create visual, audible, and/or tactile aids that will be tailored specifically to each one of the participants to ensure a coordinated, uninterrupted and seamless flow of events. Before the critical performance threshold is reached, the circulating nurse CN is made aware that a new bone removal surgical tool 16b is needed. To this end a visual aid is displayed on the display 28 and on the new surgical tool 16b that points to the appropriate surgical accessory that will be required momentarily. In other embodiments, an augmented reality aid could be superimposed on the circulating nurse's POV in their HMD 200 to indicate the location of the new surgical tool 16b. Likewise, the scrub nurse's SN display 30 may include information about the upcoming events in a gaited contextual fashion of accepting the new surgical tool 16b, receiving the consumed surgical tool 16a and handing over the replacement new surgical tool 16b to the surgeon SN. This information can similarly be provided as augmented reality aids to the HMD 200 of the scrub nurse SN. Lastly, the surgeon's SN display 24 is provided with information signaling that a tool change is required. The surgeon SN then, at his/her convenience, unmounts the consumed surgical tool 16a and immediately gets handed the replacement surgical tool 16b without delays or explicit interactions required. In other embodiments, the HMD 200 used by the surgeon may similarly provide augmented reality aids to provide such contextual event information.

Figure 11:
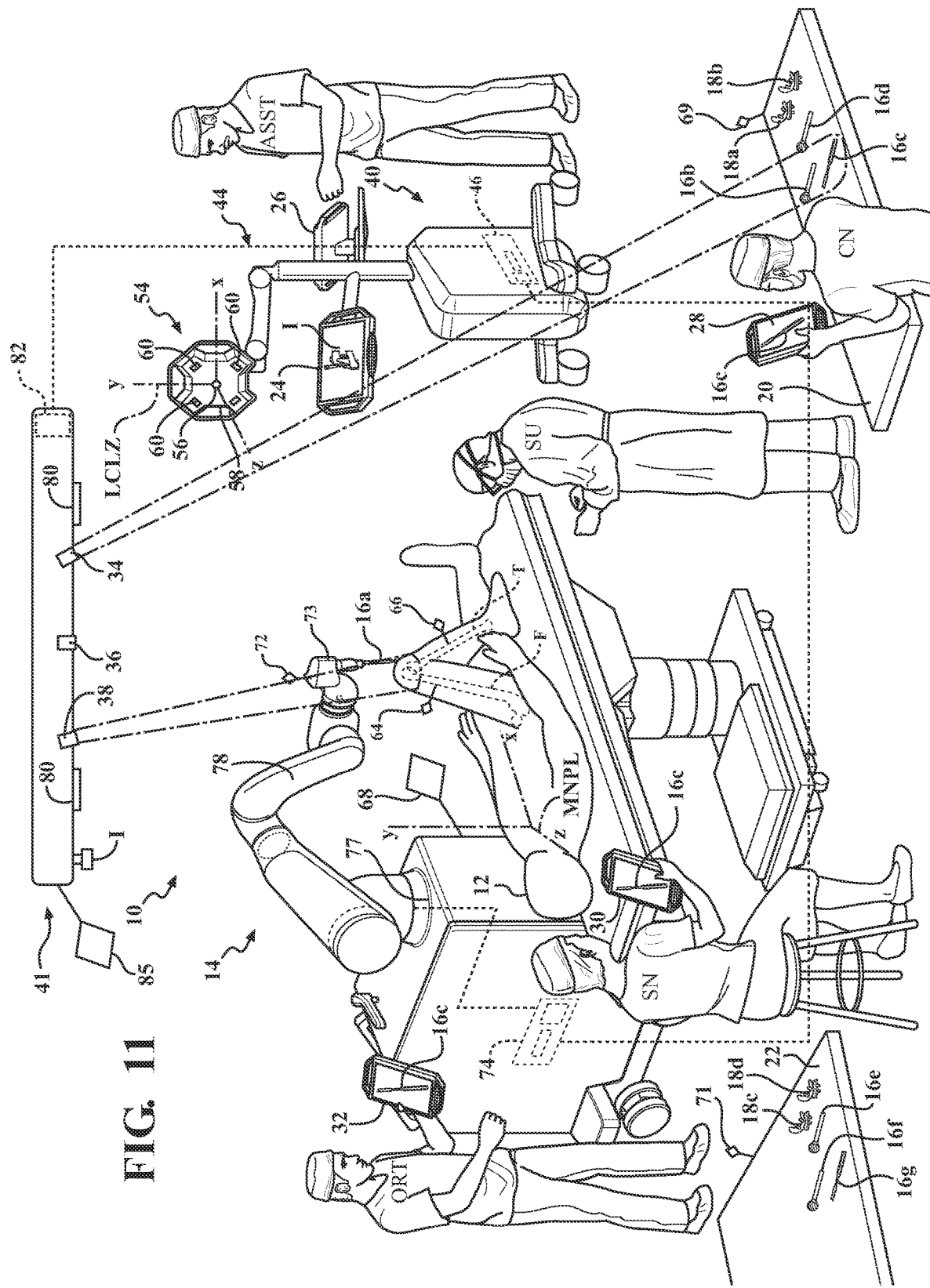
Figure 12:
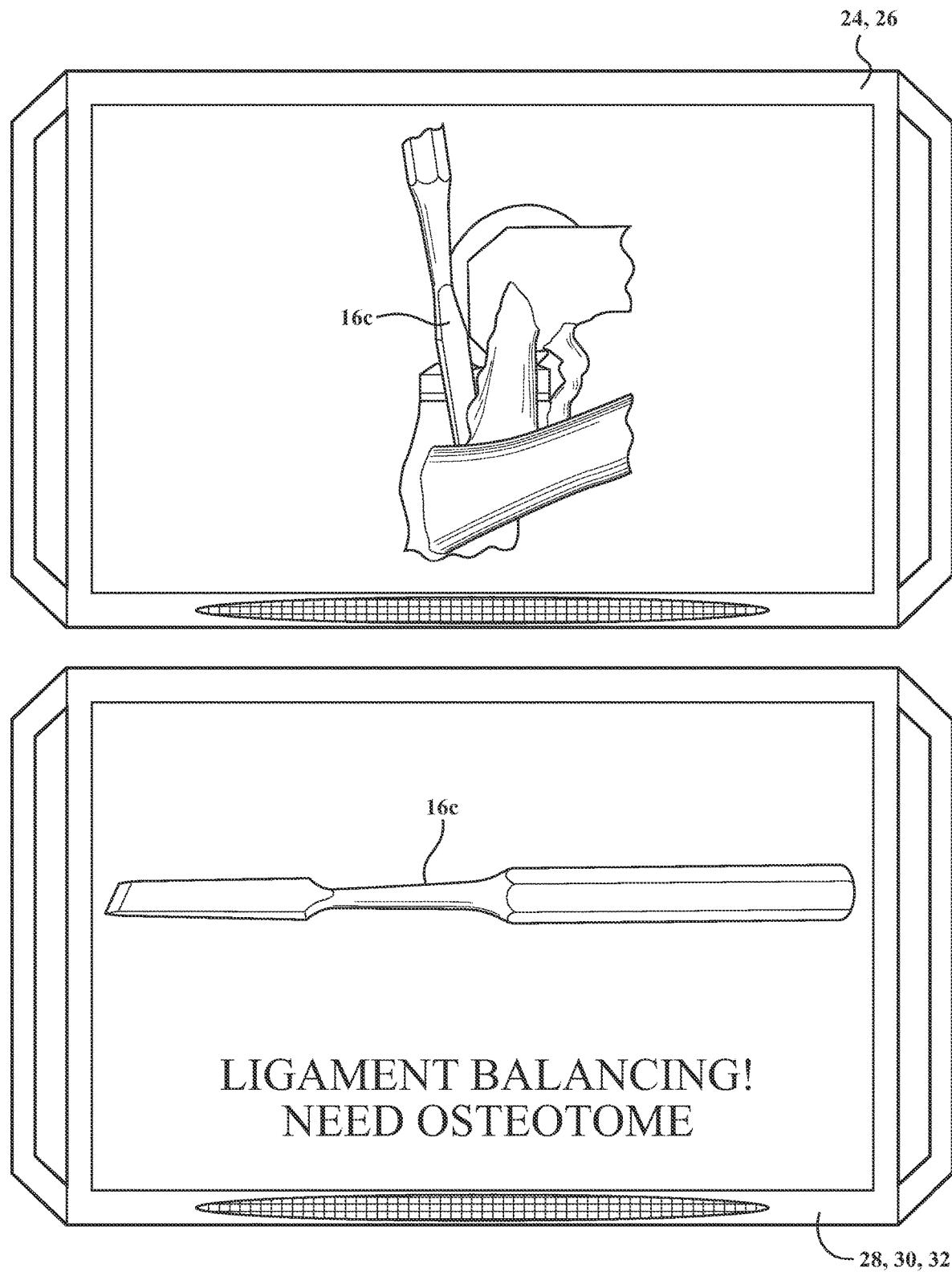

FIGS. 11 and 12 illustrate yet another example of different event information being provided to the participants in step 330*b*. When the workflow system 10 determines that ligaments need to be released and a new tool 16*c* (e.g., an osteotome) needs to be provided to the surgeon SU to release the ligaments, the workflow system 10 acts to provide the surgeon SU and the assistant ASST with first event information, which includes illustrating to the surgeon SU how to release the ligaments. The workflow system 10 provides the scrub nurse SN, the circulating nurse CN, and the operating room technician ORT with different, second event information, which includes an identity of the new surgical tool 16*c* and the location of the new surgical tool 16*c*, which can be determined when the new surgical tool 16*c* was originally laid out in the operating room during the arrangement of the objects. In many cases, various surgical tools 16*c*, 16*d*, 16*e*, 16*f*, 16*g* are made available in the operating room in anticipation of such change events. The various tools, including the surgical tool 16*c*, may be located/tracked via the navigation system 40 (e.g., via their own tracker fixed thereto or via the navigation pointer P) and/or via the machine vision system 41, and/or via other suitable location/tracking methods.

As shown in FIG. 12, the workflow controller WC causes the first event information to be shown on the displays 24, 26 to the surgeon SU and the assistant ASST, and causes the second event information to be shown on the displays 28, 30, 32 to the scrub nurse SN, the circulating nurse CN, and the OR technician ORT. Additionally, the workflow system 10, via the workflow controller WC operates two of the projectors 34, 36, 38 in the manner described above to direct visible light onto the surgical site at which the ligaments are present and onto the new surgical tool 16*c* sitting on the circulating table 20.

In some embodiments, the circulating table 20 may be outfitted with one or more light sources, such as LEDs that the workflow controller WC illuminates to indicate to the circulating nurse CN and the scrub nurse SN that the new surgical tool 16*c* needs to be readied for use (e.g., removed from a sterile package, handed from the circulating nurse CN to the scrub nurse, etc.). Additionally, the markers (e.g., active LEDs) on the tool tracker 72 may be activated by the workflow controller WC to be illuminated at the same time, flashed, etc., to indicate to the surgeon SU that the ligaments needs to be released.

The displays 24, 26, 28, 30, 32, the projectors 34, 36, 38, the HMDs 200, and any of the other information conveyor devices can be employed in alternative ways than described herein to provide different change event information to the various participants in the surgical procedure in response to a change event. The change event information may merely be indicating the location of an object via a projector or light source or providing graphics/text on one of the displays 24, 26, 28, 30, 32 about where the object is located. In other words, various forms of the change event information are possible.

Each of the controllers have one or more processors, microprocessors, microcontrollers, field programmable gate arrays, systems on a chip, discrete circuitry, and/or other suitable hardware, software, or firmware that is capable of carrying out the functions described herein. The controllers may communicate with a network via wired connections and/or one or more communication devices, which may be wireless transceivers that communicate via one or more known wireless communication protocols such as WiFi, Bluetooth, Zigbee, and the like. The controllers may be connected in any suitable manner, including in a distributed network architecture, to a bus (e.g., a controller area network), and/or one or more of the controllers may be on separate networks that communicate with each other. In some cases, the function recited as being performed by the controllers may be performed by other controllers or by a single controller. For example, the workflow controller WC may comprise any one or more of the navigation controller, the machine vision controller, the projector controller, and the manipulator controller.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A surgical workflow system for assisting a surgical procedure, the surgical workflow system comprising:
   one or both of: a surgical navigation system comprising an optical localizer and trackers to determine locations of a plurality of surgical objects and generate camera video data; and a machine vision system comprising at least one camera to determine locations of the plurality of surgical objects and generate camera video data;
   a plurality of display devices being configured to convey information to a plurality of participants in the surgical procedure and each one of the display devices being assignable to a different one of the participants; and
   a workflow controller coupled to the plurality of display devices and one or both of the surgical navigation system and the machine vision system, the workflow controller configured to;
   access a pre-scripted workflow having a plurality of workflow steps associated with the surgical procedure,
   obtain camera video data from the one or both of the surgical navigation system and the machine vision system, of the surgical procedure,
   monitor the surgical procedure from the camera video data to predict occurrence of an anticipated deviation from one or more of the workflow steps of the pre-scripted workflow,
   generate event information to address the predicted occurrence of the anticipated deviation, wherein the event information is specifically tailored to workflow responsibilities of one of the participants, and the event information comprises an action to be taken with respect to at least one surgical object, and
   automatically respond to the predicted occurrence of the anticipated deviation by being configured to transmit the event information to the display device assigned to the one of the participants of the surgical procedure.

2. The surgical workflow system of claim 1, wherein the localizer is an optical localizer and the camera video data is obtained from the camera associated with the optical localizer.

3. The surgical workflow system of claim 1, wherein the event information assists the one of the participants in taking immediate action.

4. The surgical workflow system of claim 1, wherein the event information prepares the one of the participants to deviate from the pre-scripted workflow.

5. The surgical workflow system of claim 1, wherein the surgical object is a surgical tool and the event information recommends replacing the surgical tool while the tool is in use during the surgical procedure.

6. The surgical workflow system of claim 1, wherein the workflow controller is configured to receive a pre-operative surgical plan created pre-operatively and determine the plurality of workflow steps of the pre-scripted workflow based on the pre-operative surgical plan.

7. The surgical workflow system of claim 6, wherein the workflow controller is configured to provide instructions to at least one of the participants on arranging the plurality of surgical objects based on the pre-operative surgical plan.

8. The surgical workflow system of claim 1, wherein the workflow controller receives tool data from the camera video data.

9. A computer implemented method of operating a surgical workflow system for assisting a surgical procedure, the surgical workflow system comprising one or both of: a surgical navigation system comprising a localizer and trackers to determine locations of a plurality of surgical objects and generate camera video data, and a machine vision system comprising at least one camera to determine locations of the plurality of surgical objects and generate camera video data; a plurality of display devices being configured to convey information to a plurality of participants in the surgical procedure and each one of the display devices being assignable to a different one of the participants; and a workflow controller coupled to the plurality of display devices and one or both of the surgical navigation system and the machine vision system, the workflow controller configured to perform the steps of:
  accessing a pre-scripted workflow having a plurality of workflow steps associated with the surgical procedure;
  obtaining camera video data of the surgical procedure, from the one or both of the surgical navigation system and the machine vision system;
  monitoring the surgical procedure from the camera video data;
  predicting an occurrence of an anticipated deviation from one or more of the workflow steps of the pre-scripted workflow;
  generating event information to address the predicted occurrence of the anticipated deviation wherein the event information is specifically tailored to workflow responsibilities of one of the participants, and the event information comprises an action to be taken with respect to a surgical object; and
  automatically responding to the predicted occurrence of the anticipated deviation by transmitting the event information to the display device assigned to the one of the participants of the surgical procedure through an information conveyor device.

10. The method of claim 9, wherein the localizer is an optical localizer and the method further comprises the workflow controller obtaining the camera video data from the camera associated with the optical localizer.

11. The method of claim 9, wherein transmitting the event information to the one of the participants assists the participant in taking immediate action.

12. The method of claim 9, wherein the event information prepares the one of the participants to deviate from the pre-scripted workflow.

13. The method of claim 9, wherein the surgical object is a surgical tool and the event information recommends replacing the surgical tool while the tool is in use during the surgical procedure.

14. The method of claim 9, further comprising the workflow controller receiving a pre-operative surgical plan created pre-operatively and determining the plurality of workflow steps of the pre-scripted workflow based on the pre-operative surgical plan.

15. The method of claim 14, further comprising the workflow controller providing instructions to at least one of the participants on arranging the plurality of surgical objects based on the pre-operative surgical plan.

16. The method of claim 9, further comprising the workflow controller receiving tool data from the camera video data.

* * * * *